United States Patent
Zhong et al.

(10) Patent No.: US 9,790,826 B2
(45) Date of Patent: Oct. 17, 2017

(54) SYSTEM AND METHOD FOR MONITORING LUBRICANT OF AN ENGINE

(71) Applicant: AIR CHINA LIMITED, Beijing (CN)

(72) Inventors: Dechao Zhong, Beijing (CN); Zhuping Gu, Beijing (CN); Huifeng Ding, Beijing (CN); Jiaju Wu, Beijing (CN); Lei Huang, Beijing (CN); Bingzheng Wang, Beijing (CN); Hongtao Ma, Beijing (CN); Lei Chen, Beijing (CN); Yi Zhu, Beijing (CN)

(73) Assignee: Air China Limited, Beijing (CN)

( * ) Notice: Subject to any disclaimer, the term of this patent is extended or adjusted under 35 U.S.C. 154(b) by 424 days.

(21) Appl. No.: 14/339,333

(22) Filed: Jul. 23, 2014

(65) Prior Publication Data

US 2015/0068289 A1   Mar. 12, 2015

(30) Foreign Application Priority Data

Jul. 24, 2013 (CN) .......................... 2013 1 0313815

(51) Int. Cl.
*G01N 33/487* (2006.01)
*F01M 11/12* (2006.01)
*G01N 33/28* (2006.01)

(52) U.S. Cl.
CPC ......... *F01M 11/12* (2013.01); *G01N 33/2888* (2013.01)

(58) Field of Classification Search
CPC .... G01N 33/2888; G01N 33/30; G01N 19/02; C10N 2210/02; F01M 11/10; C10M 2217/043
USPC .......................................... 73/53.05, 10, 19.11
See application file for complete search history.

(56) References Cited

U.S. PATENT DOCUMENTS

| 2,982,374 | A | * | 5/1961 | Hughes | B64D 37/34 137/43 |
|---|---|---|---|---|---|
| 4,712,372 | A | * | 12/1987 | Dickey | F01D 21/02 324/160 |
| 8,483,902 | B2 | | 7/2013 | Cornet et al. | |
| 9,540,974 | B2 | * | 1/2017 | Demaison | F01D 25/18 |
| 2009/0076677 | A1 | | 3/2009 | Walthall et al. | |
| 2009/0164056 | A1 | | 6/2009 | Cornet et al. | |
| 2011/0010069 | A1 | | 1/2011 | Payne et al. | |

(Continued)

FOREIGN PATENT DOCUMENTS

FR   2958911 A1   10/2011

OTHER PUBLICATIONS

European Search Report for Application No. 14178433.0 dated Dec. 4, 2014, 6 pages.

(Continued)

*Primary Examiner* — Eric S McCall
*Assistant Examiner* — Mohammed E Keramet-Amircola
(74) *Attorney, Agent, or Firm* — Husch Blackwell LLP

(57) ABSTRACT

The present invention relates to a system and method for monitoring lubricant of an engine. The system for monitoring lubricant of an engine comprises: a lubricant sensor, which measures lubricant quantity of the engine; a data acquisition unit, which collects the lubricant quantity of the engine from the lubricant sensor at a fixed time interval; and a message generation unit, which generates lubricant quantity monitoring messages according to the lubricant quantity of the engine collected by the data acquisition unit.

29 Claims, 15 Drawing Sheets

(56) References Cited

U.S. PATENT DOCUMENTS

| | | | |
|---|---|---|---|
| 2012/0130617 A1* | 5/2012 | Raimarckers | F01D 21/003 701/99 |
| 2013/0073171 A1* | 3/2013 | Muller | F01M 11/12 701/100 |
| 2013/0152674 A1* | 6/2013 | Noordover | G01N 3/08 73/53.05 |
| 2013/0179028 A1* | 7/2013 | Gu | G06F 17/00 701/29.4 |
| 2013/0197721 A1* | 8/2013 | Gu | B64D 45/00 701/3 |

OTHER PUBLICATIONS

Chinese office action for application No. 201310313815.0 dated May 13, 2016, 22 pages.

\* cited by examiner

ENG OIL ADDING DET RPT(027)

| | A/C ID<br>Plane No. | FROM<br>UTC Time | TO<br>Flying | FLT<br>Ground | DATE UTC<br>Flight No. |  |
|---|---|---|---|---|---|---|
| CC | aaaa | aaaa | aaaa | aaaa | aaaa | |
| | PH<br>Segment | CNT<br>Count | CODE<br>Trigger Code | APU<br>State of<br>Bleed Air<br>Valve | BLEED STATUS<br>Bleed Air Valve of<br>APU | |
| CI | 01 | 0 | 1000 | 1 | 50×0981000×52 | |
| | TAT<br>Total<br>Temperature | ALT<br>Baton Mark | CAS<br>Computed<br>Airspeed | MN<br>Mach Speed | GW<br>Total<br>Weight | CG<br>Gravity<br>Center | DMU<br>DMU Version |
| CE | 024.5 | 03771 | | | 0 | | 121CA2 |

PARAMETERS PRESET

| | 27TMR<br>End Time of<br>message | CKTMR<br>Checking Time<br>for changing of<br>the lubricant<br>amount | ENDTMR<br>The stop time of<br>the checking for<br>lubricant<br>increment | DETQ<br>Threshold Value<br>of the lubricant<br>increment | ENDTQ<br>Threshold Value<br>of the lubricant<br>increment at the<br>end of checking | OIQEXT<br>The maximum<br>time interval in<br>acquisition |
|---|---|---|---|---|---|---|
| PP | 2400 | 20 | 30 | 0.5 | 0 | 10 |

POST ENGINE SHUT DOWN FOR 10MINs

| | OIQ_ENG1<br>The lubricant amount after the stop<br>of the left engine | OIQ_ENG2<br>The lubricant amount after the stop<br>of the right engine | ENG_SHUTTIME<br>The stop time of engine |
|---|---|---|---|
| Z4 | 22.75 | 23 | aaaa |

POST ENGINE SHUT DOWN FOR 45MINs OR 5s PER NEXT MEs

| Z5 | 21.75 | 22.25 | aaaa |
|---|---|---|---|

ENGINE OIL ADDING EVENT DETECTION 3MINS INTERVAL WITHIN 10MINS

| | OIL ADD<br>Add oil or not | TIME<br>Add<br>Time | PFAD<br>The mark of<br>power-off add of oil | -20S<br>The lubricant<br>amount in the<br>first 20<br>seconds | OIQST<br>The lubricant<br>amount when<br>adding oil | OIQOLD<br>Nonvolatile memory data<br>of lubricant amount |
|---|---|---|---|---|---|---|
| AL | 0 | 0 | 0 | 0 | 0 | 21.75 |
| AR | 0 | 0 | 0 | 0 | 0 | 22.25 |
| | QDT0 | QDT1 | QDT2 | QDT3 | QDT4 | |
| ML | 0 | 0 | 0 | 0 | 0 | |
| DL | 0 | 0 | 0 | 0 | 0 | |
| | QDT0 | QDT1 | QDT2 | QDT3 | QDT4 | |
| NR | z.zz | z.zz | z.zz | z.zz | z.zz | |
| DR | -zzS | zzzzzz | zzzzzz | zzzzzz | zzzzzz | |

RATE SINCE LAST OIL ADDING(Qt/Hr)

| | CAL(G+A)<br>Lubricant<br>Consumption<br>(Sky+Ground) | CAL(AIR)<br>Lubricant<br>Consumption<br>(Sky) | OIQAV<br>The average of<br>the added amount<br>of lubricant | OIQDT<br>The total<br>amount of the<br>lubricant in<br>detection | OIQCNT<br>The number of<br>detection of<br>lubricant |
|---|---|---|---|---|---|
| CL | z.zz | z.zz | zz.zz | zz.zz | z |
| CR | z.zz | z.zz | zz.zz | zz.zz | z |

OIL ADDING MANUAL RECORD

| | QT<br>Manual input<br>lubricant amount | FH<br>Manual input flying hours of the<br>interval between adding<br>lubricant | OIL CAL<br>Manual input<br>computed lubricant<br>consumption | EMPLOY ID<br>Staff ID |
|---|---|---|---|---|
| EL | z.zz | zzz.zz | z.zz | zzzzzz |
| ER | z.zz | zzz.zz | z.zz | |

Figure 15

SYSTEM AND METHOD FOR MONITORING LUBRICANT OF AN ENGINE

TECHNICAL FIELD

The present invention relates to a monitoring system and method, in particular to a system and a method for monitoring lubricant of an engine.

BACKGROUND ART

Lubricant system is an important component for maintaining normal operation of the engine. Lubricant keeps circulating within the engine so as to provide lubrication and heat dissipation for moving parts of the engine. When an abnormality occurs to some important components of the engine, such as the bearing, the lubricant heat exchanger, sealing of oil and gas and so forth, consumption of lubricant will change abnormally. Therefore, change in the consumption of lubricant is one of the important indicators reflecting performance of the engine.

Deterioration of performance of the engine can be spotted in a timely manner through continuously monitoring short-term and long-term changes in lubricant consumption and parameters of the lubricant system, and flameout of the engine in flight caused by direct or indirect failure of the lubricant system can be avoided. Therefore, all airline companies attach great importance to the monitoring of lubricant quantity within the lubricant system of the engine. To know operation condition of the engine through calculating consumption rate of lubricant may guarantee flight safety of an aircraft.

Currently, the specific way adopted by airline companies to calculate consumption rate of lubricant is as follows: after an aircraft landed, the ground crew manually fill up the tank with the lubricant, and then manually record quantity of added lubricant. Information of quantity of the added lubricant is then input into the data input system of the airline company, and then uploaded to the data server of the airline company. Since each time the lubricant in the tank is filled up, the ratio between the quantity of the added lubricant for each time and the operation time between two consecutive additions of lubricant may reflect the lubricant consumption rate within this time period.

The existing ways involve the participation of lots of manpower. Human factors and deviations in workflow will unavoidably cause error of data, which also directly affects accuracy of the obtained lubricant consumption data. In addition, time-effectiveness in obtaining data of lubricant addition quantity cannot be guaranteed if it is input manually, and it also causes failure to obtain information of lubricant consumption in a timely manner. For example, due to requirements on arrangement of airlines operation, some aircrafts often stay overnight at other stations for days, and objective situations at other stations often affects the acquisition of lubricant consumption data.

Although each airline company has being devoted to developing a system capable of automatically monitoring lubricant of an engine all the way, no airline company has ever brought out such system. They often lack a means for timely predicting early warnings on the abnormality of parameters of the lubricant system of the engine. Once malfunction occurs to the lubricant system of the engine, major accidents such as the engine being shut down will often occur.

SUMMARY

For the above technical problems existing in prior art, there is provided according to one aspect of the present invention, a system for monitoring lubricant of an engine, comprising: a lubricant sensor, which measures lubricant quantity of the engine; a data acquisition unit, which collects said lubricant quantity of the engine from the lubricant sensor at a fixed time interval; and a message generation unit, which generates lubricant quantity monitoring messages according to the lubricant quantity of engine collected by the data acquisition unit.

For the system as described above, the lubricant quantity monitoring message comprises a lubricant quantity of flight phase monitoring message and a lubricant addition message.

For the system as described above, wherein the lubricant quantity of flight phase monitoring message comprises information reflecting the lubricant quantities after the engine is started, during the cruise phase or when the aircraft starts to descend from the cruise phase, and before the engine is shut down.

For the system as described above, wherein the lubricant quantity of flight phase monitoring message comprises information reflecting the modified lubricant quantity during the cruise phase or when the aircraft starts to descend from the cruise phase.

For the system as described above, wherein if the aircraft is in the steady-state cruise condition exceeding a preset time period, the lubricant quantity of flight phase monitoring message comprises information reflecting the lubricant quantity when the aircraft is in the steady-state cruise condition; otherwise, the lubricant quantity of flight phase monitoring message comprises information reflecting the lubricant quantity when the aircraft starts to descent from the cruise phase.

For the system as described above, wherein the lubricant quantity of flight phase monitoring message comprises information reflecting the lubricant quantity when the engine is idling before it is started.

For the system as described above, wherein the lubricant quantity of flight phase monitoring message comprises information reflecting the lubricant quantity when more than one engine are shut down.

The system as described above further comprises: a warning unit, which sends out warnings in response to an abnormality occurring to lubricant data collected by the data acquisition unit; wherein the lubricant data comprise lubricant quantity, lubricant temperature and/or lubricant pressure.

The system as described above further comprises: a communication unit, which transmits messages generated by the message generation unit to the airline company via a ground-air data link or a ground transmission apparatus.

For the system as described above, wherein the message generation unit generates a lubricant warning message in response to an abnormality occurring to the lubricant data collected by the data acquisition unit.

For the system as described above, wherein abnormality occurring to the lubricant data comprises the lubricant data exceeding its threshold value for multiple times within a prescribed time period.

For the system as described above, wherein the lubricant warning message comprises: the lubricant data and parameters of the engine as well as the threshold value of the lubricant data when an abnormality occurs to the lubricant data.

For the system as described above, wherein the threshold value of the lubricant data may be modified via an input apparatus on the aircraft.

According to another aspect of the present invention, there is provided a method for monitoring lubricant of an aircraft, comprising: collecting lubricant quantity of the engine at a fixed time interval; and generating a lubricant quantity monitoring message according to the lubricant quantity of the engine collected by the data acquisition unit.

For the method as described above, the lubricant quantity monitoring message comprises flight-phase lubricant quantity monitoring messages and lubricant addition messages.

For the method as described above, wherein the flight-phase lubricant quantity monitoring message comprises information reflecting lubricant quantities after the engine is started, during the cruise phase or when the aircraft starts to descend from the cruise phase, and before the engine is shut down.

For the method as described above, wherein the flight-phase lubricant quantity message comprises information reflecting the modified lubricant quantity of the cruise phase or when the aircraft starts to descend from the cruise phase.

For the method as described above, wherein if the aircraft is in the steady-state cruise condition exceeding a preset time period, the flight-phase lubricant quantity message comprises information reflecting lubricant quantity when the aircraft is in the steady-state cruise condition; otherwise, the flight-phase lubricant quantity monitoring message comprises information reflecting the lubricant quantity when the aircraft starts to descend from the cruise phase.

For the method described above, wherein the flight-phase lubricant quantity monitoring message comprises information reflecting the lubricant quantity when the engine is idling before being started.

For the method described above, wherein the flight-phase lubricant quantity monitoring message comprises information reflecting the lubricant quantity after more than one engine are shut down.

The method as described above further comprises: in response to abnormality occurring to the lubricant data collected by the data acquisition unit, sending out warnings; wherein the lubricant data comprise the lubricant quantity, lubricant temperature and/or lubricant pressure.

The method as described above further comprises: transmitting the lubricant monitoring message to the airline company via a ground-air data link or a ground transmission apparatus.

For the method as described above, in response to abnormality occurring to the lubricant data collected by the data acquisition unit, sending out a lubricant warning message.

For the method as described above, wherein abnormality occurring to the lubricant data comprises the lubricant data exceeding its threshold value for multiple times within a prescribed time period.

For the method as described above, wherein the lubricant warning message comprises: the lubricant data and parameters of engine and the threshold value of the lubricant data when abnormality occurs to the lubricant data.

For the method as described above, wherein the threshold value of the lubricant data may be modified via an input apparatus on the aircraft.

According to another aspect of present invention, there is provided a method for evaluating performance of an engine, comprising: obtaining lubricant quantity monitoring message of the engine during consecutive multiple legs; calculating lubricant consumption of each leg within the multiple legs; obtaining changing rule for the lubricant consumption within the multiple legs; comparing the resulting changing rule of the lubricant consumption with the changing rule of lubricant consumption when the engine works in a good state; and in response to the result of the comparison, evaluating performance of the engine.

For the method as described above, wherein the lubricant quantity monitoring message comprises flight-phase lubricant quantity monitoring messages and lubricant addition messages.

For the method as described above, wherein the lubricant consumption comprises the average consumption rate of lubricant calculated by using the lubricant addition message and/or reduced quantity of lubricant between a take-off and landing of an aircraft calculated by using the flight-phase lubricant quantity monitoring message.

For the method as described above, the comparison comprises determining whether the lubricant consumption changes by using statistic rule.

For the method as described above, the statistic rule comprises independent sample method.

For the method as described above, the evaluation of performance of an engine comprises determining whether performance of the engine enters the decline phase or failure phase, or predicting a possible malfunction of the engine.

DESCRIPTION OF DRAWINGS

Hereinafter, preferred embodiments of the present invention will be further described, taken in conjunction with the accompanying drawings, wherein:

FIG.15 is a schematic of a customized message, i.e. No.27 message, according to one embodiment of the present invention;

MODE OF THE INVENTION

Figure 1:
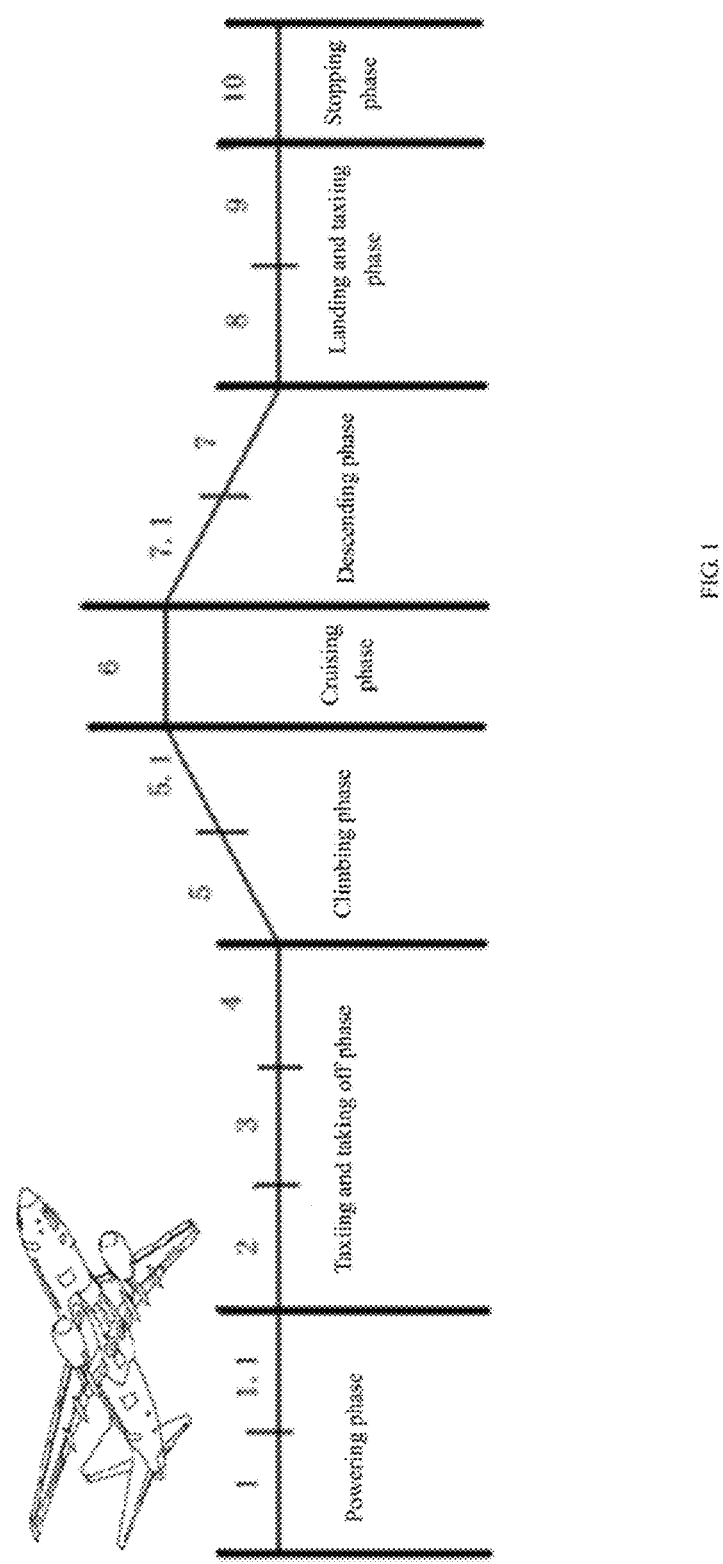
FIG.1 is a schematic of each flight phase of an aircraft.

In order to give a clearer picture of purposes, technical solutions and merits of the embodiments of the present invention, technical solutions in the embodiments of the present invention will be fully described, taken in conjunction with drawings in embodiments of the present invention. The illustrated embodiments are only a part of the embodiments of the present invention, rather than all of them. Based on embodiments in the present invention, all other embodiments a person with ordinary art in the field achieved without any creative effort shall belong to the protection scope of the present invention.

In the following detailed description, reference may be made to each figures in the specification which form a part of the present application and used for illustrating specific embodiments of the present application. In the drawings, similar symbols in different figures identify substantially similar components. With the following detail description of each specific embodiment in the present application, a person with ordinary technology and relevant knowledge in the art will be able to implement technical solutions in the present application. It shall be appreciated that other embodiments may also be used or changes may be made to the structure, logic or electric property of the embodiments of the present application.

In order to monitor each parameters of lubricant of the engine and analyze performance of the engine, the aircraft is provided with sensors of various types to collect data of lubricant of the aircraft engine. These data comprises but are not limited to: lubricant quantity, lubricant temperature and lubricant pressure. Those data constitute a part of airborne data, and may be used for monitoring, collecting, recording and distributing working condition of the lubricant system of the engine, so as to be used by flight crew and ground personnel during flight, maintenance and troubleshooting.

In airborne data systems of early aircrafts, parameters of lubricant system are collected by Flight Data Acquisition Unit (FDAU), or Flight Data Inter Face Unit (FDIU) and converted and then transmitted to Digital Flight Data Recorder (DFDR), also abbreviated as "Black Box".

Since these data cannot satisfy various requirements for operation or maintenance, the existing aircraft comprises an Aircraft Condition Monitor System (ACMS) so as to make up for deficiency of DFDR in data acquisition and appliance. Wherein, the Data Management Unit module of FDIMU, similar to FDIU, may receive parameter data from aircraft systems.

The ACMAS monitors, collects and records data of aircraft condition, and outputs preset data of aircraft condition when triggered by certain condition so as to be used by the flight crew and maintenance staff to monitor the aircraft condition and performances daily. It is referred to as Message as it data content and format may be changed by the user.

The ACMS message is generated under the control of integrated application software. A message is triggered by a certain threshold of parameters of aircraft condition or combinational logic of a multiple parameters of aircraft condition, namely, by a certain message triggering logic. The ACMS message generated by the message triggering logic designed and tested by the ACMS producer is referred to as Basic Message. Many basic messages have become standards stipulated by Civil Aviation Administration Authority. A320 aircrafts of Airbus are taken as an example and the number of ACMS basic messages they use is over 20.

A customized message may be generated by designing the ACMS message trigger logic on one's own. With the customized message, a person skilled in the art may be no longer limited by the parameters in the basic messages, and may directly face thousands of parameters of aircraft condition, which comprises lubricant data of the engine.

The new generation airborne data processing system such as the more advanced Flight Health Management system (AHM) integrate the data acquisition and data application so as to realize more complicated missions.

On the other hand, the Aircraft Communication Addressing and Reporting System data link, a main part of the air-ground data link, mainly comprises a airborne device, a far-end ground station, an air-ground data network, a ground communication network, a network management and data processing system and a user end, which may transmit information from an aircraft to a ground station, and may also transmit information from a ground station to an aircraft.

Requirement for monitoring lubricant quantity of an aircraft comprises: at first, monitoring lubricant quantity of the engine all the way; and secondly, automatically detecting lubricant addition of the engine.

Full-Course Monitoring of Lubricant Quantity of the Engine

The system and method for monitoring lubricant of an engine as described below in the present specification are illustrated by taking the ACMS system and ACARS system as examples. Other flight data processing systems or air-ground communication systems as described above, or these flight data processing systems or air-ground communication systems not included in the description of the present application may also be used to implement system and method of the present invention after undergoing appropriate adjustment.

FIG. 1 is a schematic of each phase of the operation of an aircraft. As shown in FIG.1, each phase of the operation of an aircraft comprises: powering phase, taxiing and taking off phase, climbing phase, cruising phase, descending phase, landing phase and stopping phase. Further, the engine starting phase refers to the phase from the powering phase where the aircraft is powered to the starting of the engine and then to the phase before the aircraft starts to taxi; the stopping phase of the engine refers to the phase where the engine is being stopped after the aircraft has finished taxiing, namely the aircraft stopping phase.

Since lubricant keeps circulating during the operation of the engine, and the lubricant quantity in the lubricant tank keeps changing along with the changing of status of the engine, lubricant quantity of the engine will vary greatly in different phases of the aircraft.

Figure 2:
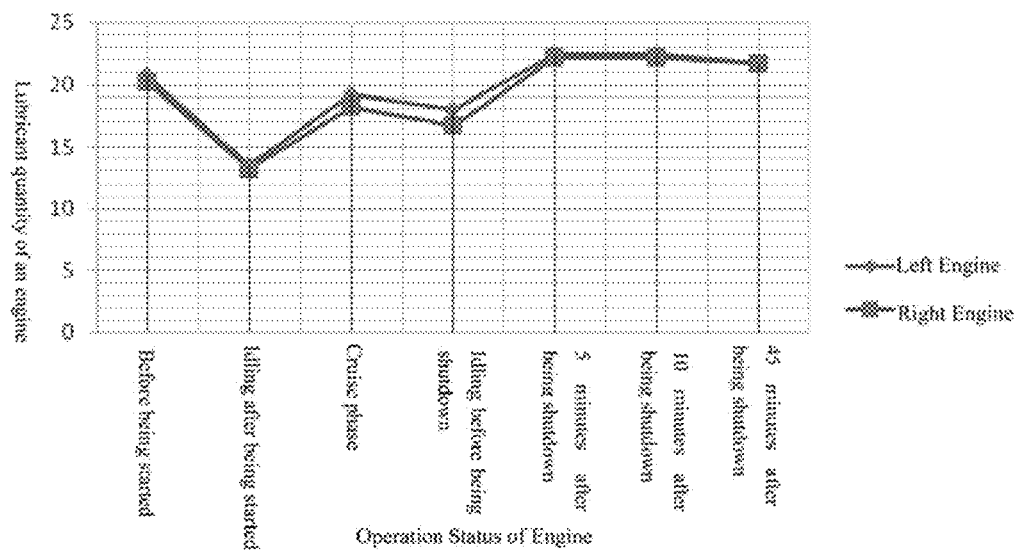
FIG.2 is a schematic showing changes of lubricant quantity of an engine as time passes by according to one embodiment of the present invention.

FIG.2 is a schematic reflecting change of lubricant quantity of an engine as time passes by according to one embodiment of the present invention. As shown in FIG.2, lubricant quantity of the engine decreases from the engine starting to be initiated to the aircraft idling after being started. Lubricant quantity of the engine starts to increase gradually from the aircraft taking off to the cruise phase. Lubricant quantity of the engine again decreases gradually during the descending phase and landing phase of the aircraft, until the time when the engine is idling before being shut down. During the 5 minutes from the time when the engine is idling before being shut down to its shut down, lubricant quantity of the engine again begins to increase gradually until reaching its maximum value. And after that, lubricant quantity of the engine gradually decreases. The so-called "idling" refers to the condition where the engine keeps operating at a minimum rotational speed. FIG. 2 is just an example of the change of lubricant quantity of a specific engine. It not only illustrates features of changes of lubricant quantity, but also reflects difficulties for monitoring lubricant quantity of an engine.

According to one embodiment of the present invention, lubricant quantity of an aircraft under several specific conditions is collected so as to reflect lubricant quantity of the engine. According to one embodiment of the present invention, data of lubricant quantity of multiple engines under the same condition are collected for later statistics and monitoring of lubricant consumption.

Figure 3:
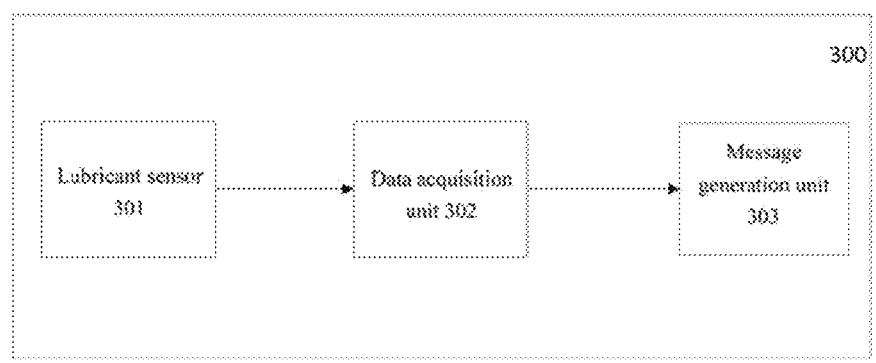
FIG.3 is a schematic of a system for monitoring lubricant of an engine according to one embodiment of the present invention.

FIG. 3 is a schematic of a system for monitoring lubricant of an engine according to one embodiment of the present invention. As shown in FIG. 3, the engine lubricant monitoring system 300 of the present invention comprises: a lubricant sensor 301, a data acquisition unit 302, and a message generation unit 303. The lubricant sensor 301 comprises one or more sensors, configured in the lubricant tank of the engine for measuring data of the engine lubricant. These lubricant data comprise but are not limited to: lubricant quantity, lubricant temperature and/or lubricant pressure. The data acquisition unit 302 collects data of engine lubricant from the lubricant sensor 301 at a fixed time interval. The time interval for the collection may be one second, ½ second, ¼ second and so forth. The data acquisition unit 302 stores the collected data in its internal or an external non-volatile storage. The message generation unit 303 generates a flight-phase engine lubricant quantity monitor message (No. 25 message), an engine lubricant warning message (No. 26 message), and/or an engine lubricant addition message (No. 27 message) according to the data of engine lubricant collected by the data acquisition unit 302. Wherein the No. 25 message reflects lubricant quantity of the aircraft during several different flight phases; the No. 26 message reflects main parameters of the engine when parameters of the lubricant of the engine exceed their limit values; and the No. 27 message reflects added amount of lubricant.

One example of data acquisition unit 302 and the message generation unit 303 of the present invention is the Flight Data Interface and Management Unit (FDIMU). The DMU of the FDIMU obtains data of various aircraft conditions, comprising lubricant data from the lubricant sensor 301, and automatically stores the data into an internal storage of the DMU or an external recorder Digital AIDS Recorder (DAR). The DMU equals to the data acquisition unit 302. The ACMS system of the FDIMU, which equals to the message generation unit 303, may generate a specific message such as No. 25-No.27 messages when certain trigger condition is met, and thus realizing real-time monitoring of the engine lubricant system. If the aircraft is not provided with the FDIMU, systems capable of executing similar functions may also be able to realize the data acquisition unit 302 and the message generation unit 303 of the present invention after undergoing proper adjustment. According to one embodiment of the present invention, the data acquisition unit 302 and the message generation unit 303 may both have an independent airborne hardware implementation.

According to one embodiment of the present invention, the engine lubricant monitoring system 300 further comprises a warning unit 304. The warning unit 304 may determine whether abnormality occurs to the lubricant data according to lubricant data of the data acquisition unit 302. If an abnormality occurs to the lubricant data, then sending out a cockpit warning; and initiating the message generation unit 303 to generate the No.26 message. According to another embodiment of the present invention, the warning unit 304 may be a part of the message generation unit 303.

According to one embodiment of the present invention, the engine lubricant monitoring system 300 further comprises a communication unit 305. The communication unit 305 may transmit the messages generated by the message generation unit 303 to a ground workstation via the ACARS or other ground-air communication systems and/or ground communication systems. Finally, these messages are transmitted to a data server of the airline company. Device on the ground workstation or the airline company automatically parses the messages, extracts lubricant data and other relevant data in the messages, and then inputs these data into the computer system of the airline company. Hence, manually recording and multiple steps of information circulating between different departments adopted in traditional way for monitoring the engine lubricant may be avoided, and accuracy and time-effectiveness for monitoring the engine lubricant may be improved.

The No. 25 message according to one embodiment of the present invention comprises the following portions: the first portion comprises message preset parameters, such as aircraft number, flight number, type of the left engine, number of the left engine, type of the right engine, number of the right engine and so forth; the second portion is the main portion of the message, comprising lubricant quantity and/or lubricant modified quantity at T1 second after the engine is started, when the engine is idling after being started, at T2 second after parameters of the engine keep stable during the cruise phase or when the aircraft starts to descend from the cruise phase, at T3 second before the engine is shut down (after the aircraft is landed), at T4, T5, and T6 second after the engine is shut down; and the third portion comprises information of the operation times of the engine, comprising in-the-air time and operation time both in the air and on the ground (in the air+ on the ground) of a single trip of the engine. Wherein, T1 is 2 to 10 seconds, preferably 5 seconds; T2 is 30 to 60 seconds, preferably 40 seconds; T3 is also 2 to 10 seconds, preferably 5 seconds; T4, T5 and T6 is 120 to 720 seconds after the engine is shut down, namely around 2 to 12 minutes; time interval for T4, T5 and T6 is around 1 minute; preferably, T4, T5 and T6 are respectively 3, 4 and 5 minutes after the engine is shut down.

Figure 4:
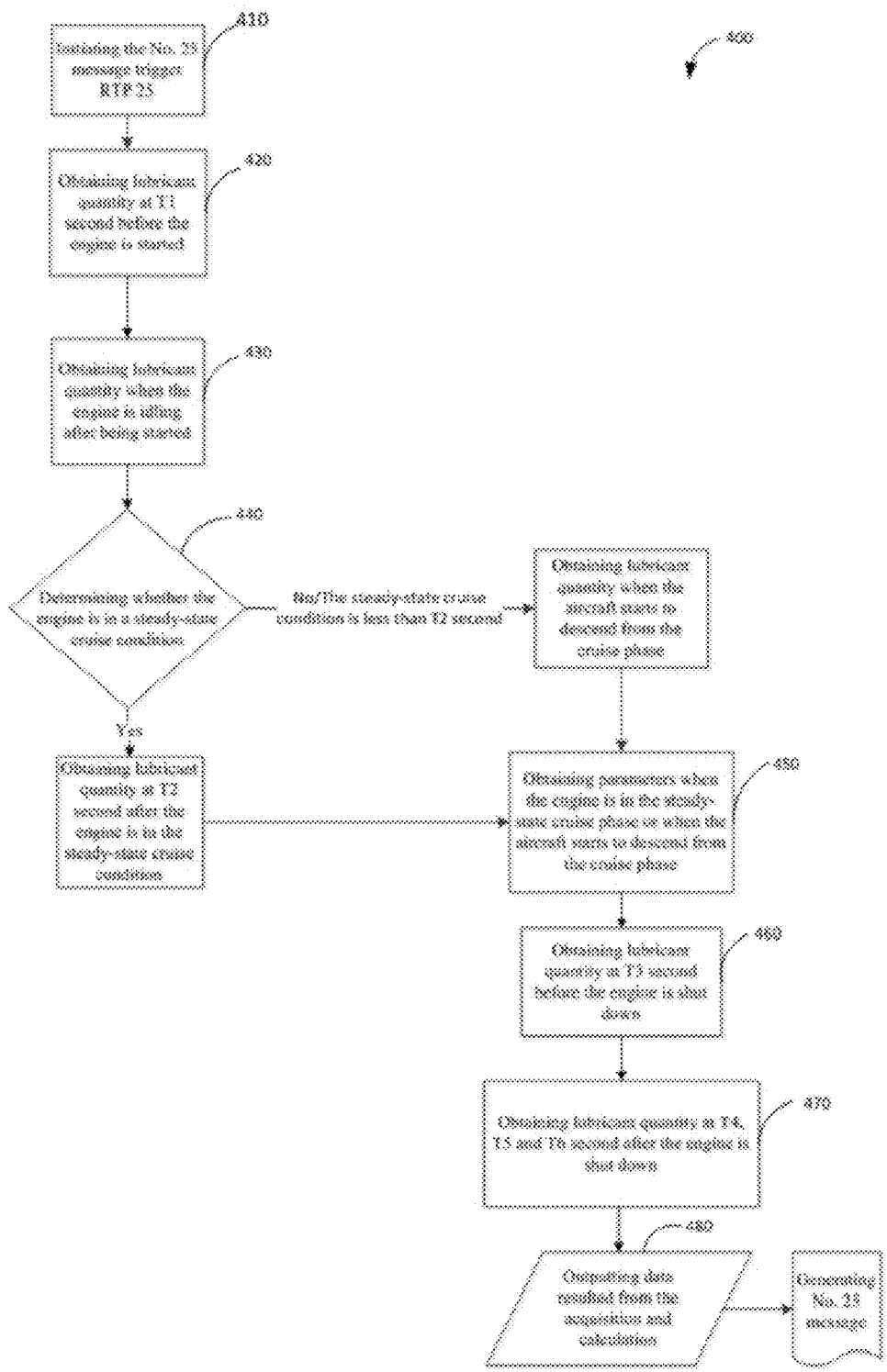
FIG.4 is a flow chart illustrating a method for generating No.25 message according to one embodiment of the present invention.

FIG. 4 is a flow chart illustrating a method for generating No. 25 message according to one embodiment of the present invention. As shown in the figure, in step 410, initiating the No. 25 message trigger RTP 25. The RTP 25 runs during all phases (PHASE ALL) of the aircraft, calculating operation time of the engine and recording value of the lubricant quantity of the engine in each phase. That is to say, the RTP 25 starts to run from the time when the engine is started. The RTP 25 records number of operation hours of the engine, air-ground flight hours and accumulative operation time from the previous addition of lubricant. In step 420, obtaining lubricant quantity at T1 second before the engine is started; in step 430, obtaining lubricant quantity when the engine is idling after being started; in step 440, determining whether the engine is in a steady-state cruise condition. If the engine is in a steady-state cruise condition, then obtaining lubricant quantity at T2 second after the engine is in the steady-state cruise condition; if the engine is not in the steady-state cruise condition all the time or the time for the engine in the steady-state cruise condition is less than T2 second, then obtaining lubricant quantity when the aircraft starts to descend from the cruise phase. When the engine is in the steady-state cruise condition, each parameter of the engine becomes stable gradually. At this time, flight condition has little influence on the lubricant quantity, which may facilitate comparison between different legs or different engines. According to one embodiment of the present invention, STABCNTP, stable parameter of the engine is used for determining whether the engine is in a steady state cruise condition. This parameter is a stable representative value of operation condition of the engine. For example, when the value of STABCNTP is 2, it represents that stable operation time of the engine lasts for 40 seconds. Further, in step 450, obtaining the following parameters of the engine when the engine is in the steady-state cruise phase or when the aircraft starts to descend from the cruise phase: lubricant temperature, N2 rotational speed of the high pressure rotator of the engine, and P3 inlet pressure of the combustion chamber, calculating the modified lubricant quantity when the engine is in the steady-state cruise phase or when the aircraft starts to descend from the cruise phase wherein the equation for calculating modified lubricant quantity of the engine is as follows:

$$OIK=OIQ*[1+(K1*OIT)+(K2*N2)+(K3*P3)]$$

Wherein, OIK is the modified lubricant quantity; OIQ is the lubricant quantity before modification; OIT is the lubricant temperature; N2 is the rotational speed of the high pressure rotator of the engine; P3 is the inlet pressure of the combustion chamber; K1, K2 and K3 are modifying coefficients, wherein $K1=-0.85*10^{-4}$; $K2=10^{-6}$; $K3=10^{-6}$.

In step 460, obtaining lubricant quantity at T3 second before the engine is shut down. In step 470, obtaining lubricant quantity at T4, T5 and T6 second after the engine is shut down. Wherein T4, T5 and T6 second are 120 to 720 seconds after the engine is shut down, namely around 2 to 12 minutes. Time interval of T4, T5 and T6 is 1 minute, and preferably T4, T5 and T6 are 3, 4 and 5 minutes respectively after the engine is shut down. In step 480, outputting data resulted from the acquisition and calculation; generating No. 25 message.

The No. 25 message fully records information of lubricant quantity during all course of each single leg of the aircraft. With the No. 25 message automatically generated by the engine lubricant monitoring system of the present invention, automatically monitoring of the engine lubricant quantity during all phases may be realized. According to information of the lubricant quantity recorded by the No. 25 message, one may further realize real-time monitoring of performance of the lubricant system and the engine.

Referring to description of No. 27 message below, the No. 27 message comprises the following information: whether lubricant is added during a flight stop; quantity of lubricant addition; lubricant quantity at 10 minutes after the engine is shut down; and lubricant quantity at 45 minutes after the engine is shut down or at 5 second before the engine is started the next time; lubricant consumption rate from the previous addition of lubricant to the lubrication addition of this time. By combining No. 25 message and No. 27 message, one will obtain changes of lubricant quantity during all courses including the flight phases and stop phases, thus realizing Phase-All monitoring of the engine lubricant.

Figure 5:
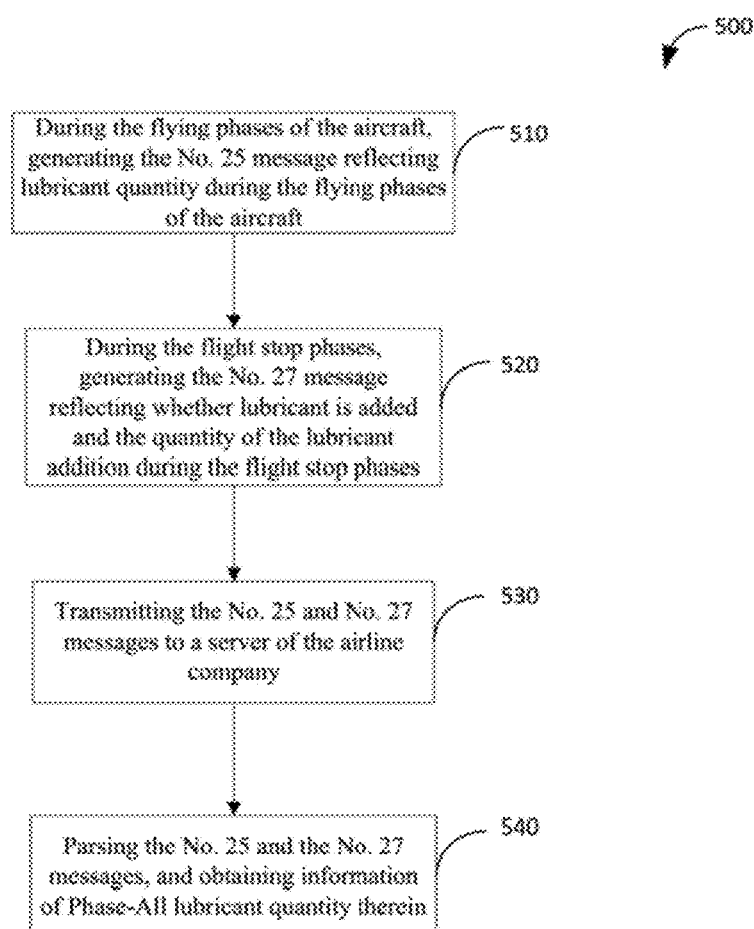
FIG.5 is a flow chart illustrating a method for monitoring lubricant of an engine according to one embodiment of the present invention.

FIG. 5 is a flow chart illustrating a method for monitoring an engine lubricant according to one embodiment of the present invention. As shown in FIG. 5, the engine lubricant monitoring method 500 comprises: in step 510, during the flying phases of the aircraft, generating the No. 25 message reflecting lubricant quantity during the flying phases of the aircraft; in step 520, during the flight stop phases, generating the No. 27 message reflecting whether lubricant is added and the quantity of the lubricant addition during the flight stop phases; in step 530, transmitting the No. 25 and No. 27 messages to a server of the airline company; and in step 540, parsing the No. 25 and the No. 27 messages, and obtaining information of Phase-All lubricant quantity therein, and thus realizing automatically Phase-All monitoring of the engine lubricant.

Figure 6:
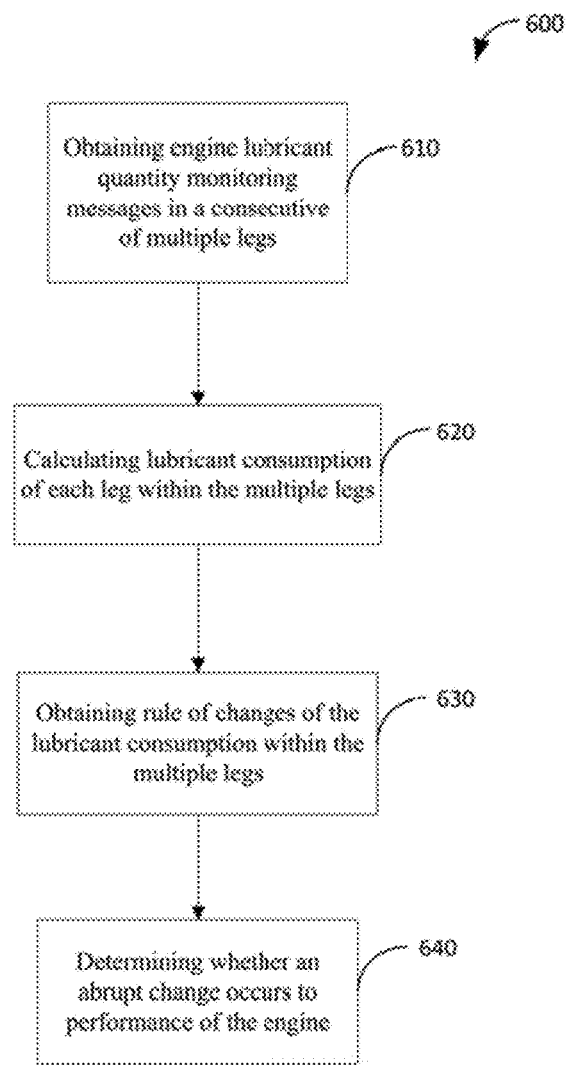
FIG.6 is a flow chart illustrating a method for monitoring performance of an engine according to one embodiment of the present invention.

FIG. 6 is a flow chart illustrating a method for monitoring performance of an engine according to one embodiment of the present invention. As shown in FIG. 6, the method 600 for monitoring performance of an engine comprises: in step 610, obtaining engine lubricant quantity monitoring messages in a consecutive of multiple legs, namely, the No. 25 message and/or No. 27 message; in step 620, calculating lubricant consumption of each leg within the multiple legs; in step 630, obtaining rule of changes of the lubricant consumption within the multiple legs; in step 640, comparing rule of changes of lubricant consumption resulted in step 630 with the rule of changes of lubricant consumption when the engine works in a good state by utilizing analyzing method such as independent sampling analysis, and determining whether the lubricant consumption still complies with the rule of changes of lubricant consumption obtained when the engine works in a good state. If the above two do not come from the same sample according to the independent sampling analysis, it means that abrupt change occurs to the lubricant consumption, such as an abrupt rapid increase in lubricant consumption. As can be appreciated by persons skilled in the art, other statistic rules may also be used herein to determine whether an abrupt change occurs to the lubricant consumption. Hence, in step 640, determining whether an abrupt change occurs to performance of the engine. The "lubricant consumption" in the embodiment of FIG. 6 may be the average lubricant consumption rate calculated by using No. 27 message, and may also be the lubricant reduction quantity between the taking-off and landing of an aircraft calculated by using No. 25 message, or other characteristic quantities of the lubricant consumption. According to one embodiment of the present invention, one may determine whether performance of the engine enters the decline phase or the failure phase, or predict any possible malfunction of the engine by using the above means.

The No. 26 message according to one embodiment of the present invention comprises the following several portions: the first portion comprises message preset parameters such as aircraft number, flight number, type of the left engine, number of the left engine, type of the right engine, number of the right engine and so forth; the second portion is the main portion of the message, comprising: engine lubricant pressure, lubricant temperature and data of lubricant quantity and threshold values of the engine lubricant pressure, lubricant temperature and lubricant quantity; the third portion is other main parameters of engines, comprising: rotational speed of the engine, temperature of inlet of the combustor and so forth.

For the system for monitoring lubricant of the engine of the present invention, it monitors each parameters of the lubricant system of engine during all phase from taking-off to landing of the aircraft in a real-time manner, such as engine lubricant pressure, engine lubricant temperature and engine lubricant quantity, and sends out warnings when abnormality occurs to the detected parameters and trigger the generation of the No. 26 message. After being generated, the No. 26 message may be transmitted to a ground receiving station via a ground-air data link and finally transmitted to the data server of the airline company, with which the airline company may be able to know operation condition of the aircraft. On the other hand, the No. 26 message may also be transmitted to the cockpit of the aircraft, being displayed on the display screen of the aircraft or printed and output via the printer of the cockpit, so as to be used by the flight crew. Apart from the data of lubricant parameters when abnormality occurs to the lubricant parameters, the No. 26 message also comprises data of the engine. Therefore, relevant person may fully understand working condition of the engine when abnormality occurs to the lubricant data, determine malfunction of the engine, and take proper response.

According to one embodiment of the present invention, the determination of whether abnormality occurs to the lubricant parameters of the engine depends on preset threshold values of relevant parameters. For different engines or an engine in different phases, the preset threshold values are also different, so as to improve sensitivity in sending out warning and reducing rate of misreport at the same time. According to one embodiment of the present invention, threshold values of the engine lubricant pressure, lubricant temperature and lubricant quantity early warnings may be directly set by the pilot via the operation interface on the aircraft, which may facilitate adjustment of condition for triggering message, and thus provide a best settings for realizing the function of early warning for lubricant parameters.

Figure 7:
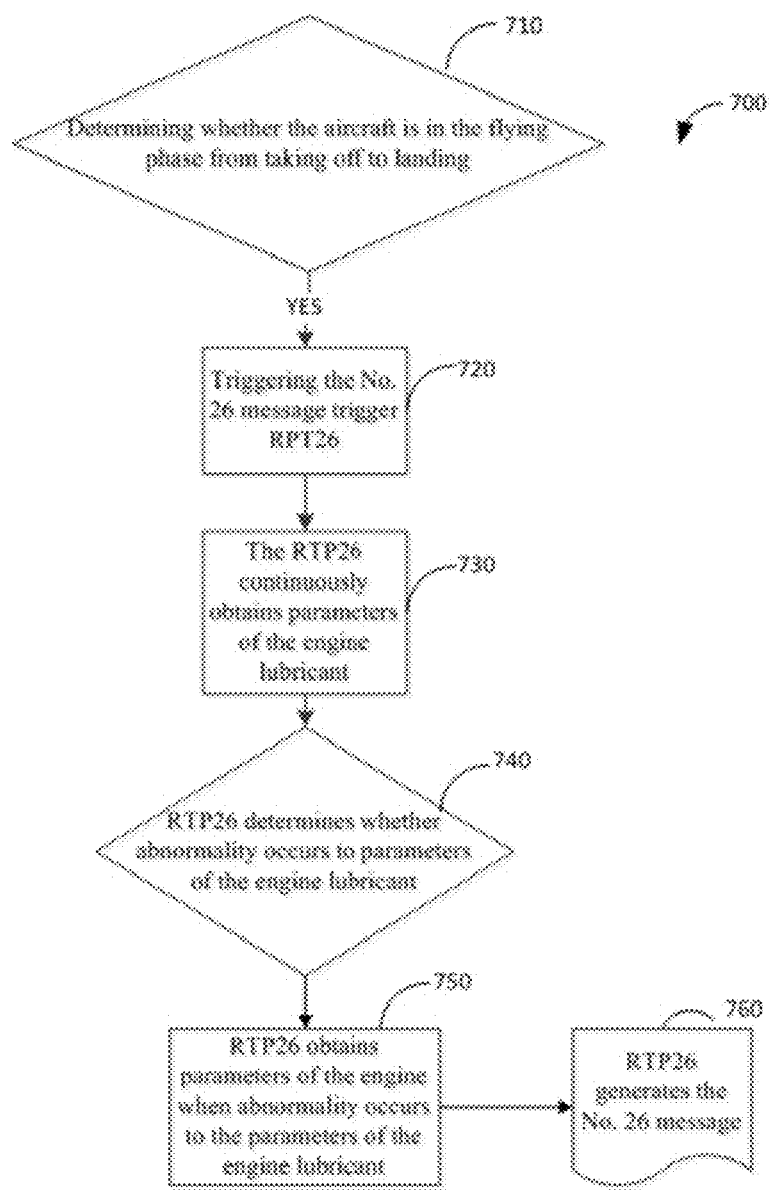
FIG.7 is a flow chart illustrating a method for generating No.26 message according to one embodiment of the present invention.

FIG. 7 is a flow chart illustrating a method for generating No. 26 message according to one embodiment of the present invention. As shown in FIG. 7, the No. 26 message generation method 700 comprises: in step 710, determining whether the aircraft is in the flying phase from taking off to landing; if the result of the determination if "YES", then in step 720, triggering the No. 26 message trigger RPT26. In step 730, the RTP26 continuously obtains parameters of the engine lubricant, these parameters comprising but not limited to engine lubricant pressure, engine lubricant temperature and engine lubricant quantity; in step 740, RTP26 determines whether abnormality occurs to parameters of the engine lubricant; if the result of the determination is "YES", then in step 750, RTP26 obtains parameters of the engine when abnormality occurs to the parameters of the engine lubricant, and in step 760, RTP26 generates the No. 26 message.

Since working condition of the engine varies relatively greatly during the operation process of the aircraft, the detected parameters of the engine lubricant, such as lubricant pressure, lubricant temperature, lubricant quantity and so forth will also change accordingly. In order to avoid wrong warnings, a step of verification may be included during the determination of whether abnormality occurs to parameters of the engine lubricant.

Figure 8:
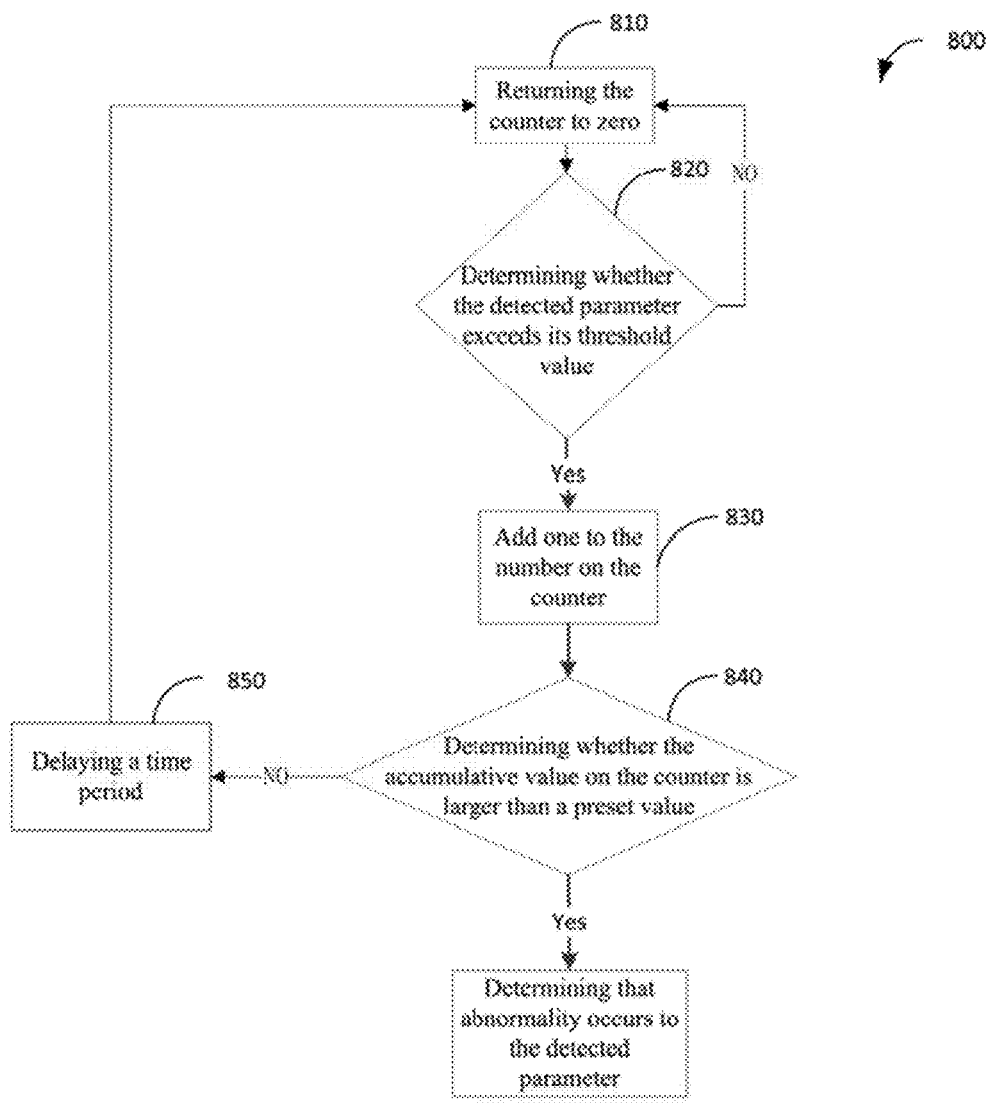
FIG.8 is a flow chart illustrating a method for determining whether an abnormality occurs to lubricant parameters according to one embodiment of the present invention.

FIG. 8 is a flow chart illustrating a method for determining whether abnormality occurs to parameters of lubricant according to one embodiment of the present invention. As shown in FIG.8, the method 800 for determining whether abnormality occurs to parameters of lubricant, comprises: in step 810, returning the counter to zero; in step 820, determining whether the detected parameter exceed its threshold value. The detected parameters comprise but are not limited to lubricant pressure, lubricant temperature, lubricant quantity and so forth. If the result is "NO", then return to step 810 and return the counter to zero; if the result if "YES", then in step 830, add one to the number on the counter; in step 840, determining whether the accumulative value on the counter is larger than a preset value; if the result is "NO", then in step 850, again return to step 820 after delaying a time period; if the result is "YES", then determining that abnormality occurs to the detected parameter. According to one embodiment of the present invention, the preset value is 3 to 5. According to one embodiment of the present invention, the delayed time period in step 850 is around 5 to 20 seconds, preferably 10 seconds.

According to the method illustrated in the embodiment of FIG.8, occurrence of abnormality of the detected parameter of lubricant is only determined to as true only when the detected parameter continuously exceeds the threshold value for a certain time period or when the detected parameter continuously exceeds the threshold value for multiple times within a very short time period. In such way, a majority of wrong warnings may be filtered out.

Compared with prior art, the system for automatically monitoring lubricant of an engine of the present invention may automatically collect data of lubricant parameters of the engine by using the message system and ground-air data link, and may automatically transmit the data to a ground workstation for analyzing. Data may be automatically uploaded into the computer information system, in such a way, manually recording and information circulating between different departments in the conventional way for monitoring lubricant of the engine may be eliminated, and accuracy and time-effectiveness for monitoring lubricant quantity of the engine may be improved. Besides, the system for automatically monitoring lubricant of an engine in the present invention also provides early warning of abnormality of lubricant parameters, and thus improving flight safety of the aircraft.

Detection of Lubricant Addition of the Engine

Although the lubricant tank of the engine is provided with a lubricant quantity sensor for detecting the lubricant quantity, it is still a very challenging task to accurately detect lubricant quantity of the engine. At first, when the aircraft is in different flight phases, liquid level in the lubricant tank may be at different positions, which makes it very difficult to detect. Secondly, during the process of adding lubricant, other after-flight maintenance work needs to be done simultaneously, for example: the aircraft may be powered off in a short time, may be dragged away, or that several additions of lubricant occur, all of them will affect the detection of lubricant. Again, due to the siphonic effect of the engine, liquid level in the lubricant tank will still change even after the completion of lubricant addition. Besides, due to factors such as that the accuracy of the lubricant sensor is not high and lubricant consumption of the engine is low, it is difficult to realize automatically detection of lubricant addition.

As shown in FIG.1, each phase of the operation of an aircraft comprises: powering phase, taxiing and taking off phase, climbing phase, cruising phase, descending phase, landing phase and stopping phase. Further, the engine starting phase refers to the phase from the powering phase where the aircraft is powered to the starting of the engine and then to the phase before the aircraft starts to taxi; the stopping phase of the engine refers to the phase where the aircraft has finished taxiing and the engine is stopped, namely the aircraft stopping phase.

According to one embodiment of the present invention, the system and method for detecting addition of lubricant of an engine of the present invention are mainly applied during the phase after the engine is shut down to automatically detect addition of lubricant, and further to calculate lubricant consumption. In circumstances where the aircraft stops during the journey for a short time period, the system and method of the present invention may also be applied during the phase when the aircraft is powering on and the engine is started. According to one embodiment of the present invention, relevant data and/or middle data resulted after calculation will be automatically stored in a non-volatile storage so as to prevent any loss due to abrupt power off, or be automatically transmitted to a ground workstation and a server of the airline company in the form of various data carriers.

According to one embodiment of the present invention, the system and method of the present invention may use the data acquisition system on the aircraft. Taking the Flight Data Interface and Management Unit (FDIMU) as an example, the FDIMU receives data of aircraft condition from airborne sensors or other devices. Data acquisition subsystem of FDIMU converts the received data of aircraft condition into digital signals for broadcasting. The Quick Access Recorder (QAR) receives and stores the broadcast data of aircraft condition, wherein, a part of the data being stored into the Flight Data Recorder (FDR), namely the "Black Box", so as to be analyzed by relevant persons after any emergency happens to the aircraft.

The data acquisition system on the aircraft obtains data of flight condition of the aircraft at a fixed frequency, comprising data of lubricant quantity from the lubricant quantity sensor. For example, the lubricant quantity sensor transmits the detected data of lubricant quantity to for example data acquisition system of FDIMU every one second or every ½ second. By recording data of lubricant quantity of different time points via the data acquisition system, the system and method of the present invention may realize automatic detection of lubricant addition. Of course, the system for detection lubricant addition may also automatically store data of lubricant quantity at different time points by itself so as to realize automatic detection of lubricant addition.

Since the existing airline company's requirements for engine lubricant service are: addition of lubricant shall be finished within a certain time period after the engine is shut down, the addition of lubricant quantity shall not be less than the lowest quantity of lubricant addition, and lubricant shall be added to the position with a full mark, the method of the present invention shall comply with the above requirements for aircraft maintenance.

Figure 9:
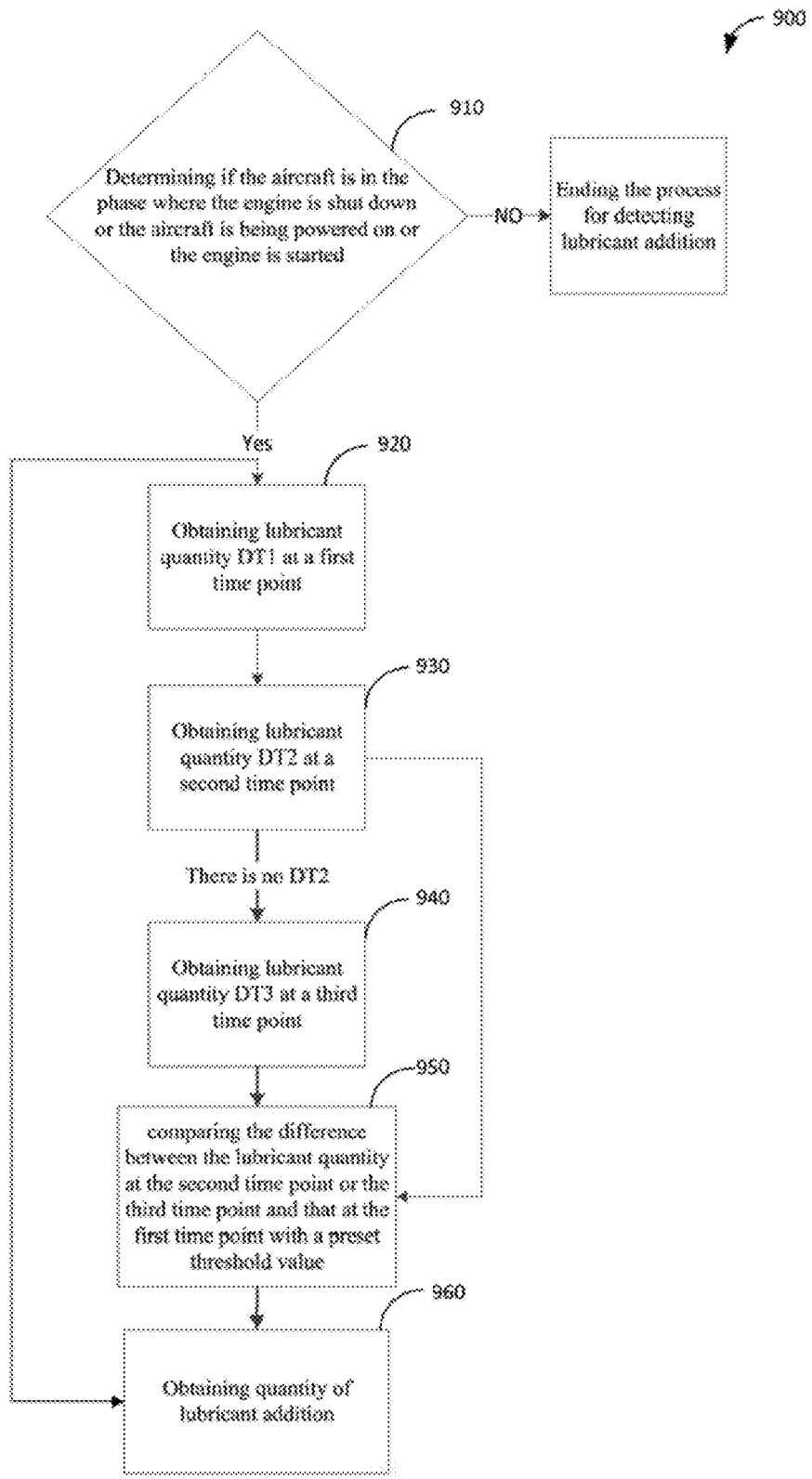
FIG.9 is a flow chart illustrating a method for detecting lubricant addition according to one embodiment of the present invention.

FIG. 9 is a flow chart illustrating a method for detecting lubricant addition according to one embodiment of the present invention. As shown in FIG.9, the lubricant addition detection method 900 comprises: in step 910, determining operation condition of the aircraft; if the aircraft is in the phase where the engine is shut down or the aircraft is being powered on or the engine is started, then initiating or carrying on the detection of lubricant addition of the present invention; otherwise, ending the process for detecting lubricant addition. In step 920, obtaining lubricant quantity at a first time point; in step 930, obtaining lubricant quantity at a second time point, wherein the second time point is later than the first time point. According to one embodiment of the present invention, the first time point is 8 to 15 minutes after the engine is shut down, preferably 10 minutes. The second time point is later than the time for adding lubricant required by the aircraft maintenance, preferably 10 to 20 minutes late. For example, if the aircraft maintenance requires that the lubricant be added within 30 minutes after the engine is shut down, then the second time point may be 45 minutes after the engine is shut down. If there is no second lubricant quantity for the second time point, then in step 940, obtaining lubricant quantity at a third time point. According to one embodiment of the present invention, the third time point is point within 3 to 10 seconds before the engine is started, preferably 5 seconds before the engine is started.

In step 950, comparing lubricant quantity at the second time point or the third time point with that at the first time point; if the increase of lubricant quantity is larger than a preset threshold value, then lubricant is added during this time period; otherwise, no lubricant is added. According to one embodiment of the present invention, the preset threshold value is the lowest quantity of addition required by aircraft maintenance or more.

After step 910, obtaining quantity of lubricant addition at step 960; or alter step 950, obtaining quantity of lubricant addition at step 960

Although when no lubricant is added, lubricant quantity at the first, second and third time points shall substantially the similar, through which one may determine whether lubricant is added, lubricant quantity in the tank will decrease gradually after the addition of lubricant due to various reasons as introduced above, the siphonic effect in particular, therefore, the accurate quantity of lubricant addition cannot be determined by directly calculating difference between the lubricant quantity at the second time point or third time point and that at the first time point.

Figure 10:
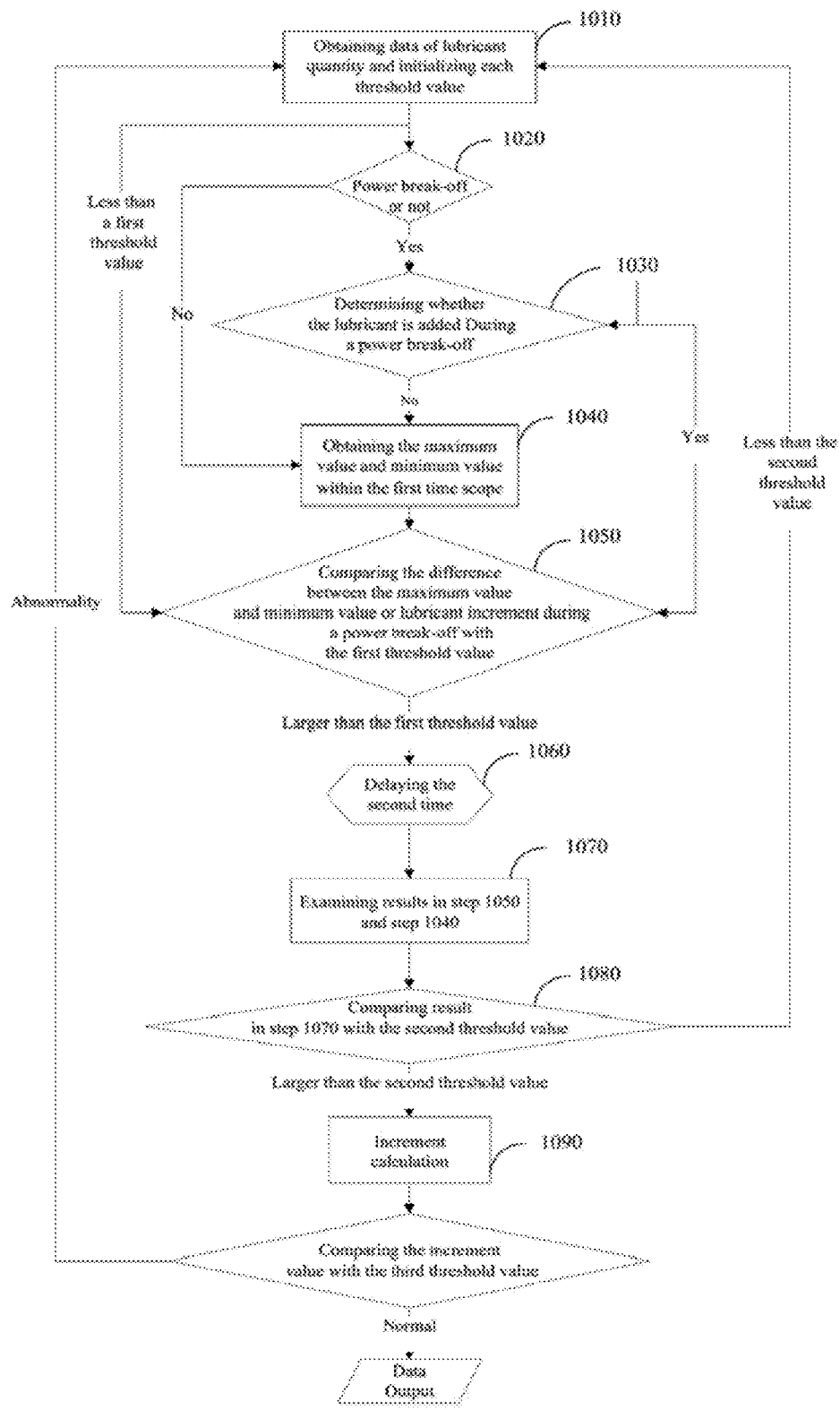
FIG.10 is a flow chart illustrating a method for obtaining lubricant addition quantity according to one embodiment of the present invention.

FIG.10 shows a way for obtaining quantity of lubricant addition according to one embodiment of the present invention. As shown in the figure, the method 1000 for obtaining quantity of lubricant addition of the present embodiment comprises: in step 1010, obtaining data of lubricant quantity and initializing each threshold value. In step 1020, detecting power break-off and determining whether a temporary power break-off happens to the aircraft and the aircraft being repowered. After an aircraft stops, its power supply will often be converted from the inner power source of the aircraft to an external power source of the airport, during which circumstance where the aircraft is powered off suddenly and then repowered might occur. This also might happen during other maintenance work of the aircraft or other situations. According to one embodiment of the present invention, the system for detecting lubricant addition of the present invention comprises a non-volatile storage. Temporary data generated during the execution of the method for detecting lubricant addition of the present invention are stored or backed up in the non-volatile storage. Hence, one may be able to determine whether the aircraft was powered off. Data will not be lost after the aircraft is powered off and the system may work normally after the aircraft is repowered.

If the aircraft is powered off and then repowered, then in step 1030, determining whether the lubricant is added when the aircraft is powered off. For example, determining whether the quantity of lubricant after the aircraft is repowered is larger than that before the aircraft is powered off. If the lubricant is added, then turn to step 1050.

If no addition of lubricant is detected in the situation where the aircraft is repowered after being powered off or during the aircraft is powered off, then in step 1040, determining quantity of lubricant of each second within a first time scope, and determining the maximum value and minimum value within the first time scope. According to one embodiment of the present invention, the first time scope comprises the time period from the beginning of the first time before the current time point to the current time point, for example, 20 to 40 seconds before the current time point, preferably 30 seconds before the current time point.

In step 1050, determining whether difference between the maximum value and the minimum value of lubricant quantity within the first time range resulted from in step 1040 is larger than a first threshold value, or whether difference between the lubricant quantity after the aircraft is repowered and that before the aircraft is powered off is larger than the first threshold value. According to one embodiment of the present invention, the first threshold value equals to or is larger than the minimum quantity of lubricant addition required by aircraft maintenance.

If it is smaller than the first threshold value, namely lubricant addition does not meet the requirement, then return to step 1020 for detecting power off of the aircraft. If it is larger than the first threshold value, then in step 1060, delaying the second time. According to one embodiment of the present invention, range of the second time is 5 to 20 seconds, preferably 10 seconds. And then, in step 1070, examining results in step 1050 and step 1040 so as to avoid fluctuation of liquid level and error in the measurement of sensors, comprising re-obtaining difference between the maximum value and minimum value of lubricant quantity according to method in step 1050, or re-obtaining increase of lubricant quantity according to method in step 1040; and then in step 1080, comparing verified data obtained in step 1070 with the second threshold value; if the verified data resulted in step 1070 is larger than the second threshold value, than it may be determined that addition of lubricant actually happens. Otherwise, return to step 1010. According to one embodiment of the present invention, the second threshold value equals to or is larger than the first threshold value.

Through steps 1020-1070, a majority of changes in data of lubricant quantity measured by lubricant sensors caused by non-lubricant addition event may be excluded via the method for detection lubricant addition of the present invention. Via the setting of the first and second threshold values, changes in lubricant quantity caused by error of sensors and disturbance with small amplitude may be filtered. Via obtaining difference between the maximum value and minimum value of lubricant quantity within the first time and extended verification, changes in lubricant quantity caused by tilting and vibration with larger amplitude of liquid level of lubricant quantity caused by dragging the aircraft may be avoided so as to more accurately detect the lubricant quantity.

If lubricant is added, then in step 1090, calculating increase in lubricant quantity, and comparing the increased value of lubricant quantity resulted from the calculation with the third threshold value; if the result of the comparison is normal, then the system outputs data of value of increase of lubricant quantity. Otherwise, return to step 1010, re-detecting event where lubricant is added.

Figure 11:
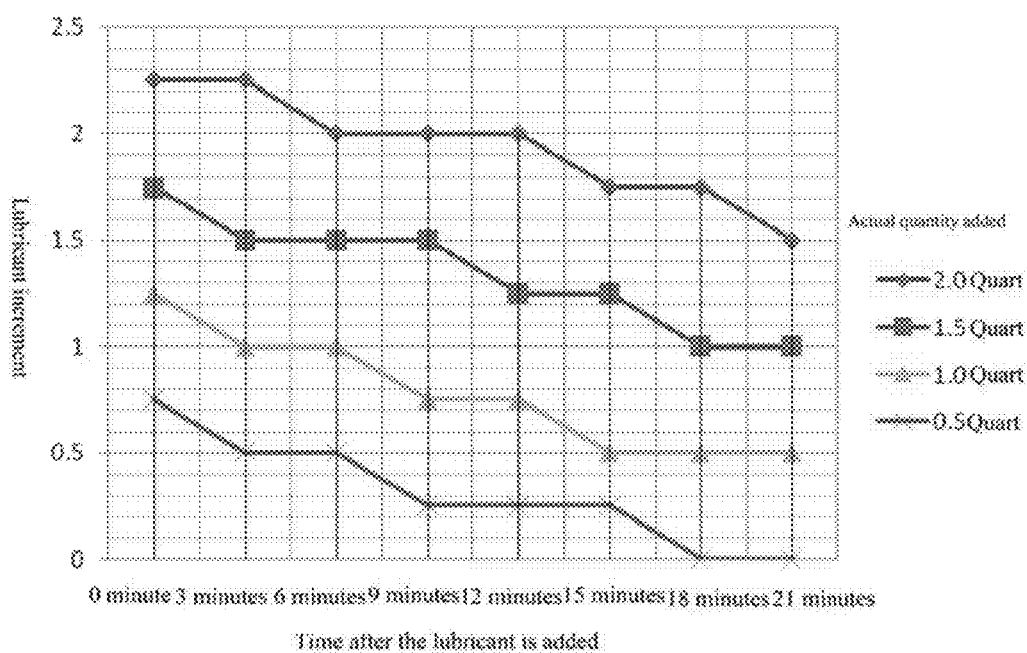
FIG.11 is a schematic reflecting change of lubricant increment after the addition of lubricant as time passes by according to one embodiment of the present invention.

FIG. 11 is a schematic reflecting change of increment of lubricant as time passes after lubricant is added according to one embodiment of the present invention. As shown in FIG. 11, after lubricant is added into the tank, lubricant quantity measured by the lubricant sensor or more visually indicated on the aircraft instrumentation is not unchanged. Part of the lubricant gradually flows back into the engine accessories due to the siphonic effect, so such change in increment of lubricant over time gradually decrease. FIG. 11 is only a specific example of change in lubricant quantity of an engine. It not only illustrates features of change of lubricant quantity of the engine, but also reflects difficulties in detecting increment of lubricant of the engine.

Figure 12:
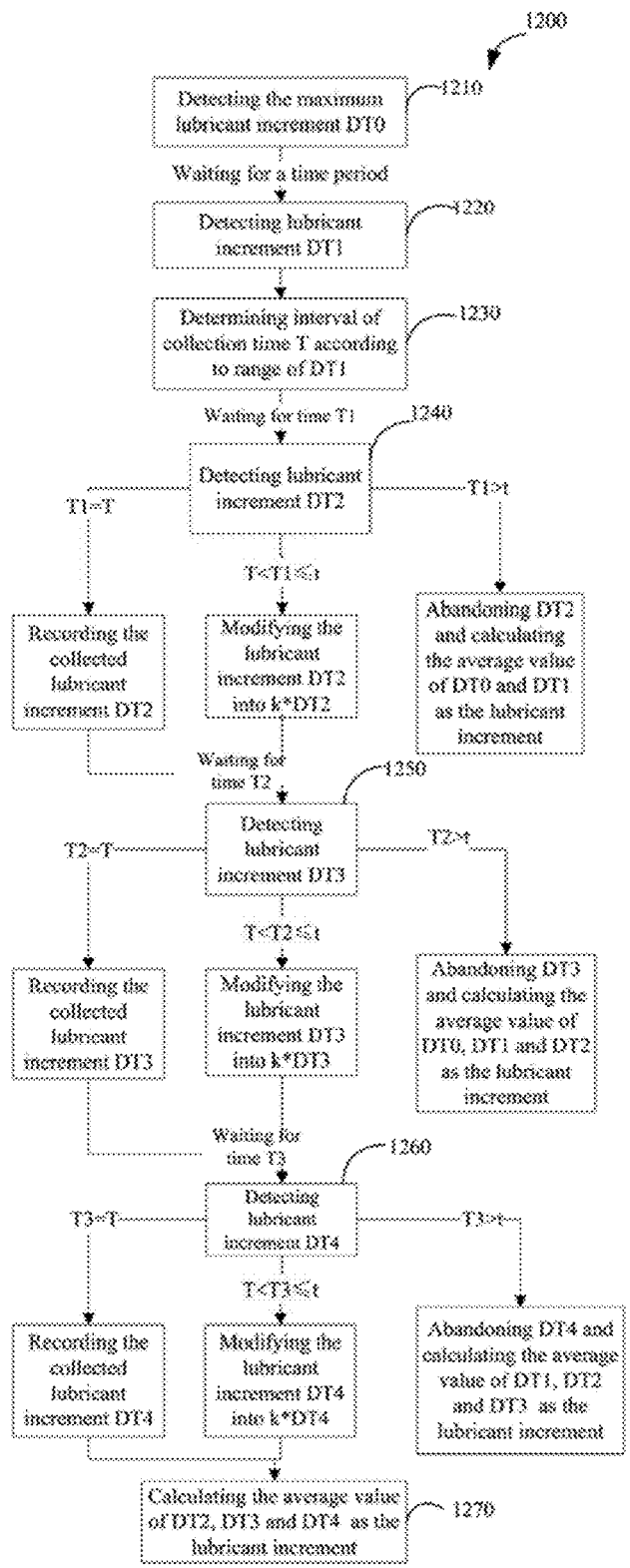
FIG.12 is a flow chart illustrating calculation of lubricant increment according to one embodiment of the present invention.

FIG. 12 is a flow chart illustrating the calculation of lubricant increment according to one embodiment of the present invention. As shown in FIG. 12, the method 1200 for calculating increment of lubricant comprises the following steps: in step 1210, detecting the maximum lubricant increment DT0. For the event of an addition of lubricant, during the process of adding lubricant, lubricant quantity in the tank keeps increasing. At a certain point, the lubricant quantity ceases to increase. Difference between the lubricant quantity at this time and that when the addition of lubricant is started or before that is the maximum lubricant increment DT0.

In step 1220, after waiting for a time period, again detecting lubricant increment DT1 and determining range of lubricant increment DT1. According to one embodiment of the present invention, range of the waiting time is 20 to 50 seconds, preferably 30 seconds.

According to one embodiment of the present invention, after the maximum lubricant increment added into the tank of the engine is obtained, disturbance or vibration of the liquid level, error in measurements and other factors may be excluded via calculating average value for multiple measurements. If time interval between each measurement is too short, it will not help to exclude those disturbing factors. However, due to siphonic effect, a part of lubricant will go back to engine assemblies such that lubricant quantity will gradually decrease as time passes by. Hence, if time interval between each measurement is too big, the siphonic effect will affect accuracy of the measurement. Therefore, in order to make the calculated lubricant increment more close to the actual quantity of lubricant addition, collection time intervals with respect to different lubricant quantities may be different correspondingly. Collection time intervals with respect to small lubricant increment may be shortened, while collection time intervals with respect to large lubricant increment may be properly extended.

In step 1230, according to range of DT1, interval of collection time T is determined. As stated above, different lubricant increment shall correspond to different interval of increment collection time. For example, for lubricant increment smaller or equivalent to 0.75QT, interval of different collections is around 1 minute in general; for lubricant increment larger than 0.75 QT and smaller than or equivalent to 1.5 QT, interval for different collections is around 2 minutes in general; for lubricant increment larger than 1.5 QT, interval for different collections is around 3 minutes in general.

In step 1240, after actually waiting for time T1, detecting lubricant increment DT2; and comparing the actually waiting time T1 with interval of collections T. If T1 equals to T, it means that the collection is normal, then recording the collected lubricant increment DT2. If T1 is larger than the maximum time delay value t, it means that the increment calculation has been interrupted too long and situations such as the aircraft being powered off might occur and the aircraft is not repowered for a long time. This is because that the increment detected at this time will not be affected to a overly small extent by the siphonic effect, and thus the detected increment DT2 is abandoned, and average value of DT0 and DT1 detected previously may serve as the final lubricant increment DT and calculation of increment is ended. If T1 is larger than collection interval T and not more than the maximum time delay value t, it means that calculation of increment is interrupted, for example by a power break-off, but the detected increment is not obviously affected by the siphonic effect due to. According to one embodiment of the present invention, the collected lubricant increment DT2 is modified at this time into k*DT2 which is served as the detection increment. Range of value of k is 1.05-1.35, preferably 1.2. According to another embodiment of the present invention, the collected lubricant increment DT2 is modified at this time into k*DT2*(AT−T)/(t−T) wherein k is the modifying coefficient, value of k is 1.35, AT is the actual time interval, t is the maximum time delay, and T is a determined time interval. According to one embodiment of the present invention, the maximum time delay t is the time for completing one addition of lubricant, and range of its value is 8-12 minutes, preferably 10 minutes.

Similarly, in step 1250, after actually waiting for time T2, detecting lubricant increment DT3; and comparing the actually waiting time T2 with interval of collections T. If T2 equals to T, then recording the collected lubricant increment DT3. If T2 is larger than the maximum time delay value t, and then the detected increment DT3 is abandoned, and average value of DT0, DT1 and DT2 detected previously may serve as the final lubricant increment DT and calculation of increment is ended. If T2 is larger than collection interval T and not more than the maximum time delay value t, according to one embodiment of the present invention, the collected lubricant increment DT3 is modified at this time into k*DT3 which is served as the detection increment. Range of value of k is 1.05-1.35, preferably 1.2. According to another embodiment of the present invention, the collected lubricant increment DT3 is modified at this time into k*DT3(AT−T)/(t−T) wherein k is the modifying coefficient, value of k is 1.35, AT is the actual time interval, t is the maximum time delay, and T is a determined time interval. According to one embodiment of the present invention, the maximum time delay t is the time for completing one addition of lubricant, and range of its value is 8-12 minutes, preferably 10 minutes.

Similarly, in step 1260, after actually waiting for time T3, detecting lubricant increment DT4; and comparing the actually waiting time T3 with interval of collections T. If T3 equals to T, then recording the collected lubricant increment DT4. If T3 is larger than the maximum time delay value t, and then the detected increment DT4 is abandoned, and average value of DT1, DT2 and DT3 detected previously may serve as the final lubricant increment DT and calculation of increment is ended. If T3 is larger than collection interval T and not more than the maximum time delay value t, according to one embodiment of the present invention, the collected lubricant increment DT4 is modified at this time into k*DT4 which is served as the detection increment. Range of value of k is 1.05-1.35, preferably 1.2. According to another embodiment of the present invention, the collected lubricant increment DT4 is modified at this time into k*DT4(AT−T)/(t−T) wherein k is the modifying coefficient, value of k is 1.35, AT is the actual time interval, t is the maximum time delay, and T is a determined time interval. According to one embodiment of the present invention, the maximum time delay t is the time for completing one addition of lubricant, and range of its value is 8-12 minutes, preferably 10 minutes.

Then, in step 1270, if DT2, DT3 and DT4 are recorded, then using average value of the detected lubricant increment DT2, DT3 and DT4 as the final lubricant increment DT, and ending the calculation of increment.

According to one embodiment of the present invention, time of addition of the final lubricant increment DT is recorded, namely adding a timestamp to the final lubricant increment DT. As such, if multiple times for adding lubricant occur, multiple lubricant increments with different timestamps will be obtained. The total amount of lubricant addition may be obtained by combining these lubricant increments.

The above embodiment fully considers that the aircraft might be powered off during the calculation of quantity of lubricant addition. For example, after the aircraft finishes working, power supply of the aircraft may be cut off or be converted to an external power source. The break-off of power supply will suspend calculation of increment. Although calculation of increment will continue after the aircraft is repowered, if time of suspension is too long, accuracy of calculation of lubricant increment will be affected as lubricant increment will change with time. The lubricant increment resulted by using the above method may avoid influence caused by siphonic effect resulted from long time beak-off of power on the calculation of lubricant increment, which may ensure accuracy of the resulted lubricant increment.

Figure 13:
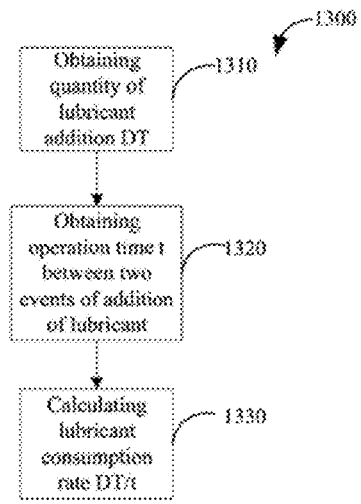
FIG.13 is a flow chart illustrating a method for calculating lubricant consumption according to one embodiment of the present invention.

FIG. 13 is a flow chart illustrating a method for calculating lubricant consumption according to one embodiment of the present invention. According to one embodiment of the present invention, the lubricant consumption calculation method 1300 comprises: in step 1310, obtaining quantity of lubricant addition DT. The methods in FIG.9, FIG.10 and FIG.12 may be applied in the present embodiment to obtain an accurate quantity of lubricant addition. Since the lubricant increment calculated by using the method of the present invention has a relatively high accuracy, the lubricant consumption rate resulted therefrom is also closer to the actual lubricant consumption of the engine.

In step 1320, obtaining operation time t between two events of addition of lubricant. Unlike traditional way of lubricant consumption calculation, the present embodiment does not use flight time of the aircraft, namely time on wing between a taking-off and a landing, as the basis for calculating lubricant consumption. This is because that the engine may have already started or is still operating before the aircraft takes off and after the aircraft is landed, deviation in the lubricant consumption calculated by using the traditional means is relative large. Especially for the monitoring of performance of an engine, the traditional way of calculating the lubricant consumption may produce wrong warnings. In step 1330, lubricant consumption rate DT/t is calculated.

The system and method for detecting addition of lubricant of an engine of the present invention may be implemented in an aircraft in various forms. According to one embodiment of the present invention, the system for detecting addition of lubricant of the present invention is implemented on the aircraft in the form of an airborne hardware.

Figure 14:
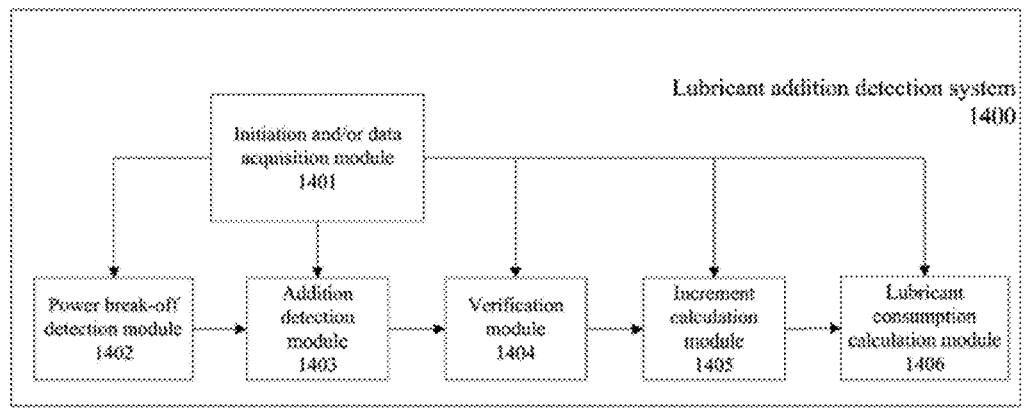
FIG.14 is a schematic of the structure of a system for detecting lubrication addition of an engine according to one embodiment of the present invention.

FIG. 14 is a schematic of the structure of a system for detecting addition of lubricant of an engine according to one embodiment of the present invention. As shown in FIG.14, the system 1400 for detecting addition of lubricant comprises multiple function modules: an initiation and/or data acquisition module 1401, a power break-off detection module 1402, an addition detection module 1403, a verification module 1404, an increment calculation module 1405 and a lubricant consumption calculation module 1406.

The initiation and data acquisition module 1401 is connected to other modules to initiate the lubricant addition detection system 1400, and assign a value to each parameter related to detection of lubricant addition. The initiation and data acquisition module 1401 may obtain data of the current quantity of lubricant from sensor in the lubricant tank or from the FDIMU in a real-time manner, and also may obtain previous data of lubricant quantity from the Quick Access Recorder (QAR) or other data sources to initiate detection of lubricant addition. According to one embodiment of the present invention, the initiation and data acquisition module 1401 may be replace by an independent initiation module and a data acquisition module.

The power break-off detection module 1402 determines and process power break-off of the aircraft. If the addition of lubricant is performed when the aircraft is powered off, the power break-off module 1402 determines whether lubricant is added during the power break-off after the aircraft is repowered. For example, determining whether difference between the lubricant quantity after the aircraft is repowered and that before the power break-off is larger than the minimum quantity of lubricant addition required by aircraft maintenance.

The addition detection module 1403 detects the addition of lubricant. For example, the addition detection module 1403 collects, at every second, lubricant quantity within the range of 30 seconds, and then determines whether difference between the maximum value and the minimum value of the lubricant quantity within the 30 seconds is larger than the minimum quantity of lubricant addition required by the aircraft maintenance.

The verification module 1404 is connected to the addition detection module 1403 to eliminate wrong determination of the system. For example, after a certain time period is extended, the verification module 1404 recalculates the difference between the maximum value and the minimum value of the lubricant quantity within the 30 seconds is larger than the minimum quantity of lubricant addition required by the aircraft maintenance.

The increment calculation module 1405 is connected to the verification module 1404 to obtain an accurate quantity of lubricant addition. The increment calculation module 1405 obtains quantity of lubricant addition by calculating average value of multiple measurements, and time interval between different measurements varies according to different lubricant increment. For small lubricant increment, the time interval between different measurements is even shorter, while time interval for larger lubricant increment is longer. If the aircraft is powered off during obtaining quantity of lubricant addition, then stopping the measurement. According to one embodiment of the present invention, the increment calculation module 1405 utilizes timestamp updating algorithm to solve the problem of data calculation caused by multiple additions of lubricant, and finally obtains lubricant increment relatively approaching the actual quantity of lubricant addition.

The lubricant consumption calculation module 1406 is connected to the increment calculation module 1405 to obtain lubricant consumption rate of the engine according to the resulted lubricant increment and the detected operation time of the engine, so as to monitor performance of the engine in a real-time manner.

According to one embodiment of the present invention, the lubricant addition detection system 1400 further comprises a lubricant addition event detection module for obtaining lubricant quantity at for example 10 minutes after the engine is shut down, 45 minutes after the engine is shut down or 5 seconds before the engine is started, comparing lubricant quantity at 10 minutes after the engine is shut down and that at 45 minutes after the engine is shut down or at 5 seconds before the engine is started, and determining whether there is a lubricant addition event.

According to one embodiment of the present invention, the system for detecting lubricant addition of an engine of the present invention may be implemented on an airborne computer in the form of software. Similar to the embodiment in FIG.14, the system for detecting lubricant addition may comprise multiple function modules: an initiation and/or data acquisition module, a power break-off detection module, an addition detection module, a verification module, an increment calculation module and a lubricant consumption calculation module. Functions of these modules are similar to that of each module in the embodiment in FIG.14, and thus will not be repeatedly illustrated here.

According to one embodiment of the present invention, the system for detecting lubricant addition of an engine of the present invention is implemented on the Aircraft Condition Monitoring System (ACMS) of the FDIMU.

The ACMAS monitors, collects and records data of aircraft condition, and outputs preset data of aircraft condition when triggered by certain condition so as to be used by the flight crew and maintenance staff to monitor the aircraft condition and performances daily. It is referred to as Message as it data content and format may be changed by the user.

The ACMS message is generated under the control of integrated application software. A message is triggered by a certain threshold of parameters of aircraft condition or combinational logic of a multiple parameters of aircraft condition, namely, by a certain message triggering logic. The ACMS message generated by the message triggering logic designed and tested by the ACMS producer is referred to as Basic Message. Many basic messages have become standards stipulated by Civil Aviation Administration Authority. A320 aircrafts of Airbus are taken as an example and the number of ACMS basic messages they use is over 20.

A customized message may be generated via composing the ACMS message trigger logic on one's own. With the customized message, a person skilled in the art may be no longer limited by the parameters in the basic messages, and may directly face thousands of parameters of aircraft condition, which comprises lubricant quantity of the engine.

FIG.15 is a schematic of a customized message, namely the No.27 message, according to one embodiment of the present invention. As shown in the figure, the No.27 message comprises four portions: the first portion comprises message preset parameters, such as aircraft number, flight number, leg and so forth, and message ending time 27TMR, lubricant changing verification time CKTMR, lubricant increment determination stopping time ENDTMR, lubricant addition increment threshold value DETQ, lubricant addition ending determination increment threshold value ENDTQ, collection maximum time interval OIQEXT. The second portion comprises: lubricant quantity at $10^{th}$ minute after the engine is shut down and the recorded time and lubricant quantity at $45^{th}$ minute after the engine is shut down or at $5^{th}$ second before the next time the engine is started and the recorded time. The third portion is the main portion of No.27 message, which may be divided into 4 sections. Section 1 is information relating to lubricant addition, comprising: mark of lubricant addition, starting time point of the addition, mark of lubricant addition during a power break-off, lubricant quantity at $20^{th}$ second before the addition, starting lubricant quantity, historical data of lubricant quantity. Section 2 is information of lubricant addition of the left engine, comprising: lubricant increment of the left engine and the corresponding recording time. Section 3 is information of lubricant addition of the right engine, comprising: lubricant increment of the right engine and the corresponding recording time. Section 4 is information of lubricant consumption. If lubricant is added, that calculated lubricant consumption of the engine is displayed, comprising lubricant consumption on air and lubricant consumption on air and on the ground. Section 4 also comprises the following information: average value of the lubricant increment, lubricant increment and amount of effective lubricant increment. In order to be compatible with existing way of manually recording lubricant addition, and further determining information of lubricant addition, Section 4 of No. 27 message comprises: if the quantity of lubricant addition is manually input in the cockpit, then recording quantity of lubricant addition, hours of the engine in air, lubricant consumption and identification number of employee.

Figure 16:
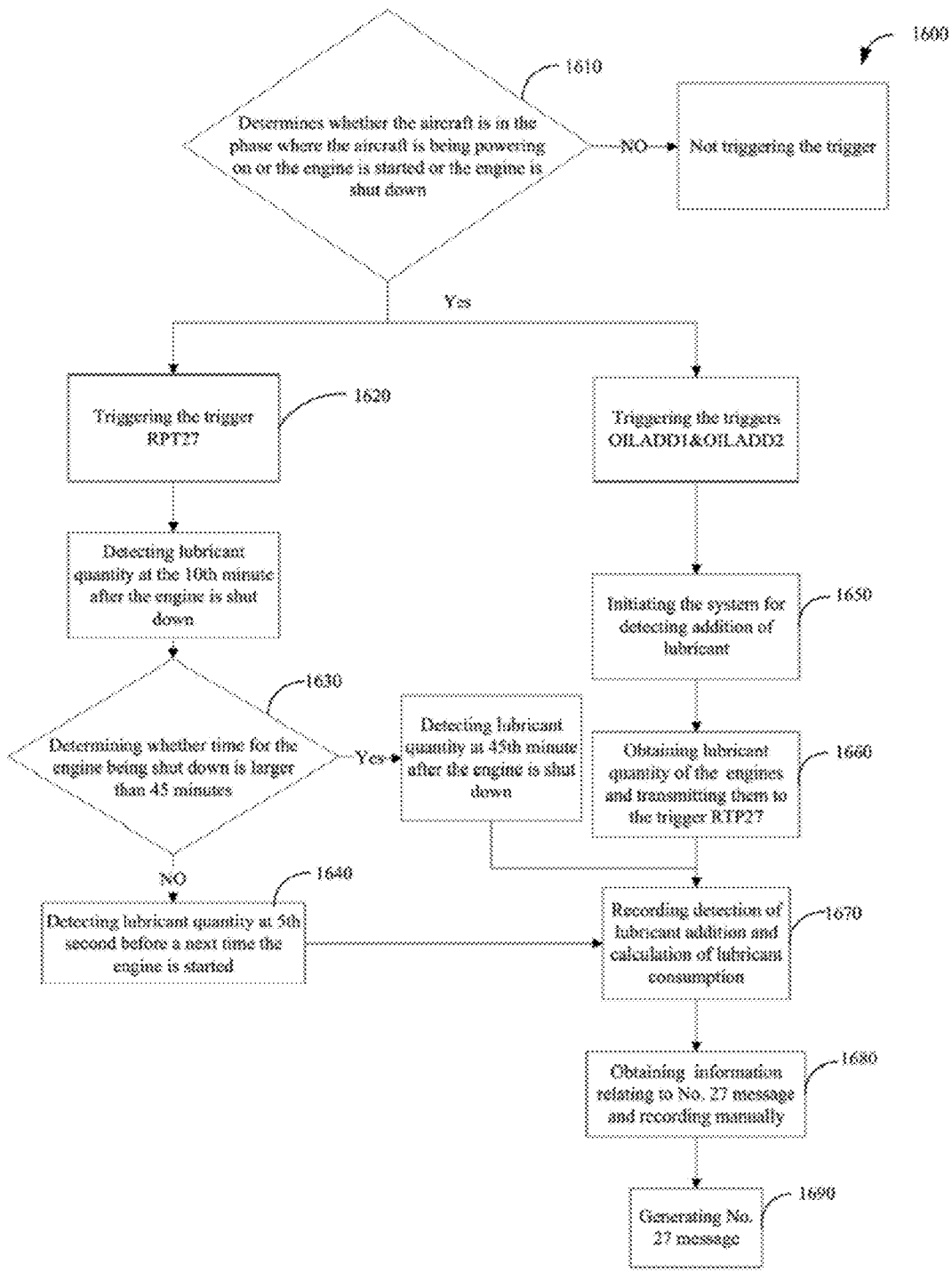
FIG.16 is a flow chart illustrating a method for generating No.27 message according to one embodiment of the present invention.

FIG.16 is a flow chart illustrating a method for generating No. 27 message according to one embodiment of the present invention. As shown in FIG.16, the method 1600 for generating No. 27 message comprises the following steps: in step 1610, basic trigger (or process) in the ACMS determines whether the aircraft is in the phase where the aircraft is being powering on or the engine is started or the engine is shut down. If the result is "No", then do not trigger any trigger, and do not initiate the system for detecting lubricant addition; if the result is "YES", then trigger the No. 27 message trigger RTP27 and the first and second lubricant increment trigger OILADD1 and OILADD2.

The basic trigger in the ACMS is a process that the ACMS system keeps running after being started. Each trigger for generating various messages is triggered by the basic trigger. The process for generating No. 27 message may be triggered by adding the trigger logic of No. 27 message into the basic trigger, for example whether the aircraft is in the phase where the aircraft is powered on or the engine is started or the engine is shut down and corresponding following actions. According to one embodiment of the present invention, the No. 27 message trigger RTP27 and the first and second lubricant increment trigger OILADD1 and OILADD2 may also be triggered by other triggers such as trigger for monitoring operation condition of the aircraft.

In step 1620, the trigger RPT27 detects lubricant quantity 10 minutes after the engine is shot down. In step 1630, the trigger RPT27 detects whether time for the engine being shut down is larger than 45 minutes, if the result of the determination is "YES", then detecting lubricant quantity at 45$^{th}$ minute after the engine is shut down; if the result of the determination is "NO", then in step 1640, the trigger RPT27 detects lubricant quantity at 5$^{th}$ second before a next time the engine is started. At the same time, in step 1650, the trigger OILADD1 and OILADD2 initiate the system for detecting addition of lubricant, wherein the trigger OILADD1 used for detecting lubricant increment of the left engine, while the trigger OILADD2 used for detecting lubricant increment of the right engine. This system for detecting addition of lubricant may be implemented in the form of an airborne hardware, and may also be implemented on an airborne computer in the form of a software, or be implemented in the form of a software on ACMS. In step 1660, lubricant quantity of the left and eight engines may be obtained and transmitted to the trigger RTP27. If multiple additions of lubricant exit, then the final total amount of lubricant increment is transmitted. In step 1670, the trigger RTP 27 recording detection of lubricant addition and calculation of lubricant consumption to obtain the added lubricant quantity and data of lubricant consumption. In step 1680, the trigger RPT27 obtains preset parameters of No. 27 message and information relating to addition of lubricant, and manually record of lubricant addition. Finally, in step 1690, the trigger RPT27 generates No. 27 message.

Figure 17:
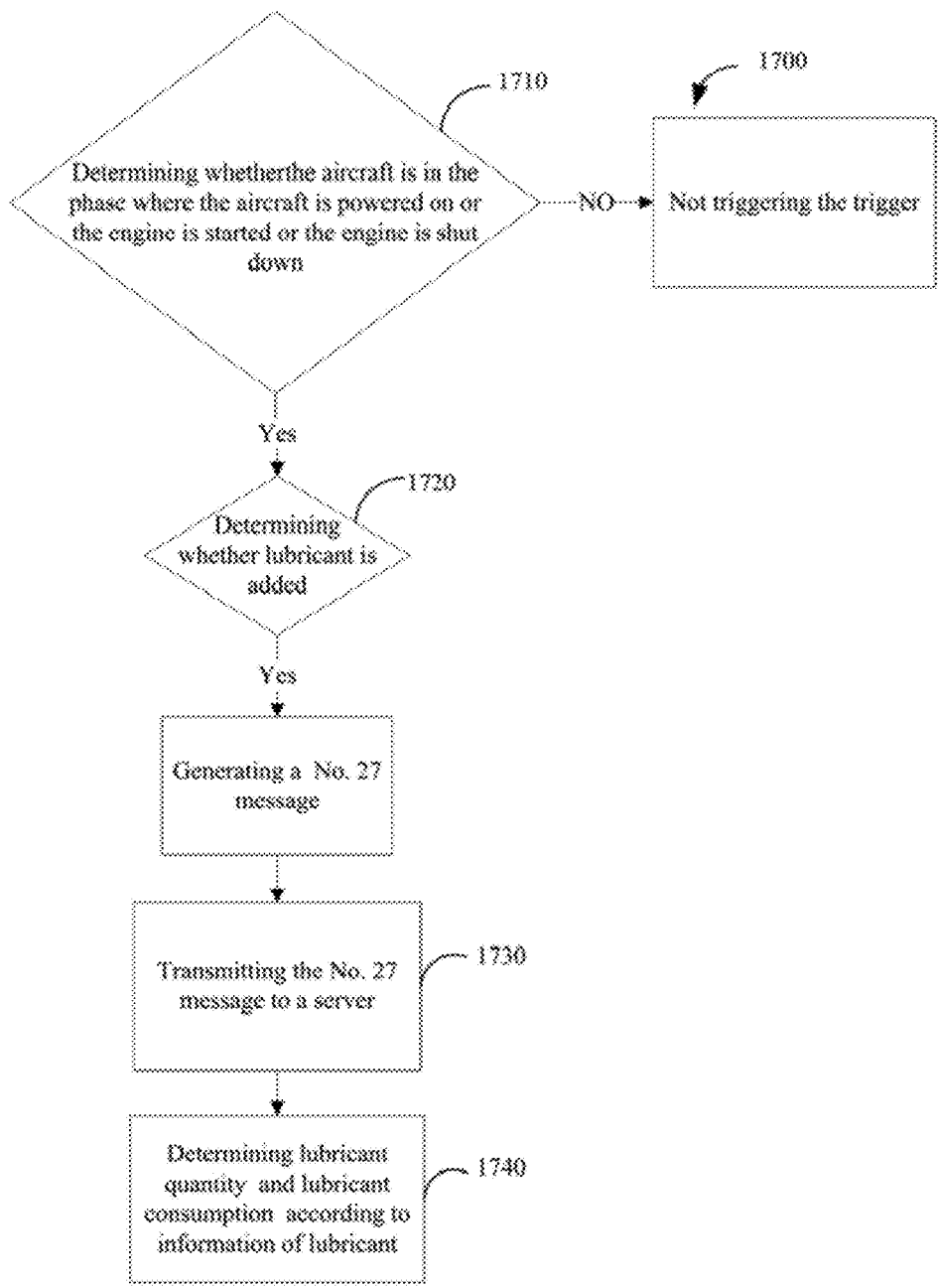
FIG.17 is a schematic of a method for monitoring lubricant of an engine according to one embodiment of the present invention.

FIG. 17 is a schematic of a method for monitoring lubricant of an engine according to one embodiment of the present invention. As shown in FIG. 17, the method 1700 for monitoring lubricant quantity of an engine comprises: in step 1710, determining whether the aircraft is in the phase where the aircraft is powered on or the engine is started or the engine is shut down; in step 1720, determining whether lubricant is added during this time period; if lubricant is added, then generating a corresponding No. 27 message; in step 1730, transmitting the No. 27 message to a server of the airline company via a ground transmission device or the ACARS system; and in step 1740, determining lubricant quantity in the current engine and lubricant consumption during the previous journey according to information of lubricant increment recorded in the No. 27 message and the existing information of lubricant, so as to realize monitoring lubricant quantity of the engine. According to one embodiment of the present invention, the No. 27 message may automatically enter into the system for monitoring lubricant quantity of the engine so as to realize automatically monitoring of lubricant quantity of the engine.

Compared with prior art, the system for detecting lubricant addition of the present invention may automatically collect lubricant quantity of an engine and calculate lubricant consumption rate of the engine, and transmit the same to a ground station for analyzing, which solves problem in accuracy and time-effectiveness in traditional way of monitoring lubricant consumption of the engine, improve flight safety. Meanwhile, it may reduce effect caused by a power break-off to the detection of data, greatly improving reliability of the detected data.

The above embodiments are only described for illustrating the present invention, rather than limiting the present invention. Persons in the relevant art may make various changes and variations without departing from the scope of the present invention. Therefore, all equivalent technical solutions shall also belong to scope of disclosure of the present invention.

We claims:

1. A system for monitoring lubricant of an engine, comprising:
   a lubricant sensor, which measures lubricant quantity of an engine;
   a data acquisition unit, which collects lubricant quantity of the engine from the lubricant sensor at a fixed time interval; and a message generation unit, which generates a flight-phase lubricant quantity monitoring message and a lubricant addition message according to the lubricant quantity of the engine collected by the data acquisition unit;
   wherein the lubricant addition message comprises information reflecting whether lubricant is added during a flight stop phase and quantity of lubricant added during the flight stop, and wherein the quantity of lubricant added are automatically determined according to the lubricant quantity of the engine collected by the data acquisition unit during the flight stop phase.

2. The system of claim 1, wherein the flight-phase lubricant quantity monitoring message comprises information reflecting lubricant quantities after the engine is started, during the cruise phase or when the aircraft starts to descend from the cruise phase, and before the engine is shut down.

3. The system of claim 2, wherein the flight-phase lubricant quantity monitoring message comprises information reflecting modified lubricant quantities during the cruise phase or when the aircraft starts to descend from the cruise phase.

4. The system of claim 2, wherein if the aircraft is in a steady-state cruise condition exceeding a present time period, the flight-phase lubricant quantity monitoring message comprises information reflecting lubricant quantity when the aircraft is in a steady-state cruise condition; otherwise, the flight-phase lubricant quantity monitoring message comprises information reflecting lubricant quantity when the aircraft starts to descend from the cruise phase.

5. The system of claim 1, wherein the flight-phase lubricant quantity monitoring message comprises information reflecting lubricant quantity when the engine is idling before it is started.

6. The system of claim 1, wherein the flight-phase lubricant quantity monitoring message comprises information reflecting lubricant quantity after more than one engine are shut down.

7. The system of claim 1 further comprises: a warning unit, which sends out warnings in response to abnormality occurring to lubricant data collected by the data acquisition unit; wherein the lubricant data comprise lubricant quantity, lubricant temperature and/or lubricant pressure.

8. The system of claim 7, wherein the message generation unit generates a lubricant warning message in response to abnormality occurring to lubricant data collected by the data acquisition unit.

9. The system of claim 8, wherein abnormality occurring to the lubricant data comprises the lubricant data exceeding its threshold value for multiple times within a prescribed time period.

10. The system of claim 9, wherein the lubricant warning message comprises: the lubricant data and parameters of the engine as well as the threshold value of the lubricant data when the abnormality occurs to the lubricant data.

11. The system of claim 1 further comprises: a communication unit, which transmits the flight-phase lubricant quantity monitoring message and the lubricant addition message generated by the message generation unit to the airline company via a ground-air data link or a ground transmission apparatus.

12. The system of claim 1, wherein the threshold value of the lubricant data may be modified via an input apparatus on the aircraft.

13. A method for monitoring lubricant of an engine, comprising: collecting lubricant quantity of the engine at a fixed time interval;
and generating a flight-phase lubricant quantity monitoring message and a lubricant addition message according to the lubricant quantity of the engine;
wherein the lubricant addition message comprises information reflecting whether lubricant is added during a flight stop phase and quantity of the lubricant added during the flight stop, and wherein the quantity of lubricant added are automatically determined according to the lubricant quantity of the engine collected by the data acquisition unit during the flight stop phase.

14. The method of claim 13, wherein flight-phase lubricant quantity monitoring message comprises information reflecting lubricant quantities after the engine is started, during the cruise phase or when the aircraft starts to descent from the cruise phase, and before the engine is shut down.

15. The method of claim 14, wherein the flight-phase lubricant quantity monitoring message comprises information reflecting modified lubricant quantity during the cruise phase or when the aircraft starts to descend from the cruise phase.

16. The method of claim 14, wherein if the aircraft is in a steady-state cruise condition exceeding a preset time period, the flight-phase lubricant quantity monitoring message comprises information reflecting lubricant quantity when the aircraft is in the steady-state cruise phase; otherwise, the flight-phase lubricant quantity monitoring message comprises information reflecting lubricant quantity when the aircraft starts to descend from the cruise phase.

17. The method of claim 13, wherein the flight-phase lubricant quantity monitoring message comprises information reflecting lubricant quantity when the engine is idling before it is started.

18. The method of claim 13, wherein the flight-phase lubricant quantity monitoring message comprises information reflecting lubricant quantity when more than one engine are shut down.

19. The method of claim 13 further comprises: in response to abnormality occurring to lubricant data collected by the data acquisition unit, sending out warnings; wherein the lubricant data comprise lubricant quantity, lubricant temperature and/or lubricant pressure.

20. The method of claim 13 further comprising: transmitting the flight-phase lubricant monitoring message and the lubricant addition message to the airline company via a ground-air data link or a ground transmission apparatus.

21. The method of claim 13 further comprising, in response to abnormality occurring to lubricant data collected by the data acquisition unit, generating a lubricant warning message.

22. The method of claim 21, wherein the abnormality occurring to the lubricant data comprises the lubricant data exceeding its threshold value for multiple times within a prescribed time period.

23. The method of claim 22, wherein the lubricant warning message comprises: the lubricant data and parameters of engine as well as the threshold value of the lubricant data when the abnormality occurs to the lubricant data.

24. The method of claim 22, wherein the threshold value of the lubricant data may be modified via an input apparatus on the aircraft.

25. A method for evaluating performance of an engine, comprising:
obtaining flight-phase lubricant quantity monitoring messages and lubricant addition messages of the engine in multiple consecutive legs according to lubricant quantity of the engine collected in the multiple consecutive legs, wherein the lubricant addition messages comprise information reflecting whether lubricant is added during a flight stop phase and quantity of the lubricant added during the flight stop, and wherein the quantity of lubricant added are automatically determined according to the lubricant quantity of the engine collected by the data acquisition unit during the flight stop phase;
calculating lubricant consumption of each leg within the multiple legs;
obtaining changing rule of lubricant consumption within the multiple legs;
comparing the resulted changing rule of the lubricant consumption with the changing rule of lubricant consumption obtained when the engine works in a good state; and
in response to result of the comparison, evaluating performance of the engine.

26. The method of claim 25, wherein the lubricant consumption comprises average consumption rate of lubricant calculated by using the lubricant addition message and/or reduced quantity of lubricant between a take-off and landing of the aircraft calculated by using the flight-phase lubricant quantity monitoring message.

27. The method of claim 25, wherein the comparison comprises determining whether the lubricant consumption changes by using statistic rule.

28. The method of claim 27, wherein the statistic rule comprises independent sample method.

29. The method of claim 25, wherein the evaluation of performance of the engine comprises determining whether performance of the engine is in the decline phase or failure phase, or predicting possible malfunction of the engine.

* * * * *